(12) United States Patent
Zou et al.

(10) Patent No.: US 6,727,275 B2
(45) Date of Patent: Apr. 27, 2004

(54) PYRROLIDINONE DERIVATIVES

(75) Inventors: Dong Zou, Concord, MA (US); Olivier Dasse, Marlborough, MA (US); Janelle Evans, Newton, MA (US); Paul Higgins, Danvers, MA (US); Jeremy Kintigh, Waltham, MA (US); Rama Kondru, South Weymouth, MA (US); Eric Schwartz, Wakefield, MA (US); Laurent Knerr, Braine-le-Chateau (BE); Hai-Xiao Zhai, Bedford, MA (US)

(73) Assignee: UCB, S.A./N.V., Brussels (BE)

( * ) Notice: Subject to any disclaimer, the term of this patent is extended or adjusted under 35 U.S.C. 154(b) by 0 days.

(21) Appl. No.: 10/255,494

(22) Filed: Sep. 26, 2002

(65) Prior Publication Data

US 2003/0149081 A1 Aug. 7, 2003

Related U.S. Application Data

(63) Continuation-in-part of application No. 09/970,140, filed on Oct. 3, 2001
(60) Provisional application No. 60/400,807, filed on Aug. 1, 2002.

(51) Int. Cl.[7] ..................... C07D 207/26; A61K 31/40
(52) U.S. Cl. ..................... 514/423; 548/540; 548/544; 514/424
(58) Field of Search ................. 548/540, 544; 514/423, 424

(56) References Cited

PUBLICATIONS

Bertha et al (1998): Tetrahedron, vol. 54(50), 15227–15242, (CA PLUS document No. 130: 124913).*

* cited by examiner

Primary Examiner—Joseph K. McKane
Assistant Examiner—Golam M M Shameem
(74) Attorney, Agent, or Firm—McDonnell Boehnen Hulbert & Berghoff

(57) ABSTRACT

The present invention provides pharmaceutical compositions and novel compounds useful in the treatment of conditions mediated by CCR2, MCP-1 or the interaction thereof. The compounds of the present invention are pyrrolidinones and pyrrolidine-thiones.

21 Claims, No Drawings

PYRROLIDINONE DERIVATIVES

This is a continuation-in-part of application Ser. No. 09/970,140, filed Oct. 3, 2001, and claims the benefit of U.S. Provisional Application No. 60/400,807, filed Aug. 1, 2002.

BACKGROUND OF THE INVENTION

1. Field of the Invention

The invention relates to the field of pharmaceutical compounds in particular pyrrolidinones and pyrrolidine-thiones and analogs thereof.

The invention further concerns processes for preparing these pharmaceutical compounds, compositions containing them and their use for the treatment and prevention of disease.

2. Summary of the Related Art

Chemokines (chemotactic cytokines) are a large class of proteins that share structural homology and possess chemotactic activity for a variety of cell types (Luster, A. (1998), N. Eng. J. Med. 338:436; Kim, C. and Broxmeyer, H. (1999), J. Leuk. Biol. 65: 6.). They are divided into four groups based on the number and positioning of the first two cysteines of their sequence. The two major groups are the CC or beta chemokines (having two adjacent cysteines) and the CXC or alpha chemokines (X representing a single amino acid in between the cysteines). Examples of the former group include MIP-1α, MIP-1β, RANTES, MCP-1, (Kim, ibid; Strader, C. et al (1995), FASEB J. 9: 745; Salcedo, R. et al (2000), Blood 96: 34), Eotaxin, TARC, MDC, MIP-3α, MIP-3β and I-309. Examples of the latter group include IL-8, NAP-1, MGSA-α, β, and γ, ENA-78, IP-10, Mig, I-TAC, SDF-1 and BLC. In addition to the CC and CXC chemokines, two other types of chemokine are known, each consisting of a single known chemokine. Fractalkine is a CX3C type, having three amino acids between its first two cysteines, and lymphotactin is a C type chemokine having only one cysteine in the N-terminal domain.

Numerous chemokine receptors have been identified and extensively characterized with respect to the chemokines they bind and the cells on which they are expressed. These receptors (CCRs, CXCRs, CX3CRs and CRs, depending on which type of chemokine they bind) exhibit a significant degree of sequence homology. Chemokine receptors are members of the large receptor family known as G-protein coupled receptors (GPCRs)(Strader, C. et al (1995), FASEB J. 9: 745), which are characterized by having seven-transmembrane helical domains and being functionally associated with heterotrimeric GTP-binding proteins (G-proteins). The existence of such a variety of chemokines (over 40) and chemokine receptors (at least 19 have been identified), in addition to their differential expression on specific cell types, provides for enormous diversity and specificity of ligand-receptor interactions. Consequently, the biological functions mediated by these proteins are diverse and complex.

MCP-1 is a chemokine produced by a number of cell types, including macrophages, mast cells, epithelial cells, endothelial cells, and fibroblasts and astrocytes. It is a potent chemoattractant for a number of different types of immune cells, such as monocytes, macrophages, activated T cells, basophils, and immature dendritic cells. MCP-1 has also been shown to induce biological responses in endothelial cells and astrocytes (Salcedo, R. et al (2000), Blood 96: 34; Dorf, M. et al (2000), J. Neuroimmunol. 111: 109). MCP-1 binds to CCR2 and, to date, no other high affinity receptor specific for MCP-1 has been confirmed. CCR2 is constitutively expressed in many immune cells and is also up-regulated under inflammatory conditions. CCR2 is also expressed in the human monocytic cell line THP-1 (Van Riper, G. et al (1993), J. Exp. Med. 177: 851).

It is well established that MCP-1 is a central factor in the immunoregulation of inflammatory responses. Numerous studies in animals have demonstrated the direct effect of MCP-1 on the infiltration of immune effector cells in vivo. For example, transgenic mice expressing MCP-1 in specific tissues exhibit an enhanced localized infiltration of monocytes in those tissues (Gu, L. et al (1997), J. Leuk. Biol. 62: 577; Gunn, M. et al (1997), J. Immunol. 158: 376). Injection of MCP-1 protein into animals has also been shown to induce the infiltration of basophils and T cells (Taub, D. et al (1995), J. Clin. Invest. 95: 1370; Conti, P. et al (1997), Int. Immunol. 9: 1563; Kuntsfeld, R. et al (1998), J. Invest. Dermatol. 111: 1040). Knockout mice lacking either MCP-1 (Lu, B. et al (1998), J. Exp. Med. 187: 601) or CCR2 (Kurihara, T. et al (1997), J. Exp. Med. 186: 1757; Kuziel, W. et al (1997), Proc. Nat. Acad. Sci. USA 94: 12053) exhibit a reduction in the extravasation and tissue infiltration of monocytes and macrophages in response to inflammatory stimuli. Neutralization of MCP-1 with monoclonal antibodies has been shown to inhibit the infiltration of monocytes (Ajuebor, M. et al (1998), J. Leuk. Biol. 63: 108) and T cells (Rand, M. et al (1996), Am. J. Pathol. 148: 855) in experimentally-induced models of inflammation in animals.

The immune response to pathogens initially involves presentation of antigen to CD4$^+$ T cells followed by clonal expansion and differentiation of the T cells into Th1 and Th2 subpopulations (Paul, W. (1992), in Inflammation, J. Gallin, I. Goldstein, and R. Snyderman (eds), pp 775–790. Raven Press; Abbas, A. et al (1996), Nature 383: 787). The two T cell subsets produce different types of cytokines that mediate the induction of different types of immune responses. Th1 cells produce IFNα, IL-2, IL-12, and TNFβ which function to generate antiviral immunity in the form of cytotoxic T cells, natural killer cells, and antibody subclasses that mediate antibody dependent cellular cytotoxicity (ADCC). Th2 cells produce IL-4, IL-5, IL-10, and IL-13, which generate allergic and anti-parasitic immune responses by inducing the proliferation and activation of eosinophils and mast cells and the synthesis of IgE antibodies. MCP-1, in addition to its direct effect on the migration of monocytes and T cells, has been shown to play a part in the regulation of T cell responses. MCP-1 has been shown to bias differentiation of activated T cells towards the Th2 phenotype, both in vitro and in vivo (Karpus, W. et al (1997), J. Immunol. 158: 4129; Gu, L. et al (2000), Nature 404: 407).

The production and biological activity of MCP-1 makes it a central player in the pathogenesis of inflammatory diseases by acting at many levels. For example, in atopic asthma, exposure to allergen induces immediate release of MCP-1 by activated mast cells and MCP-1 production at later times by epithelium and endogenous macrophages. MCP-1 subsequently induces the chemotaxis of T lymphocytes, macrophages and basophils into the challenged tissues and induces T cells to differentiate to the Th2 subtype. This results in the generation of IL-4 and IL-5 and, subsequently, the production of IgE and the proliferation and migration of eosinophils. These coordinated biological responses, centrally mediated by MCP-1, lead to the infiltration and activation of immune effector cells, increased sensitization of mast cells in the lung, and maintenance of the asthmatic condition.

It is evident that CCR2 is an appropriate target for inhibiting the excessive inflammatory responses that contribute to disease. The present invention is based on the discovery of compounds that antagonize CCR2. By antagonizing this receptor, the compounds block the biological effects of MCP-1 and thus inhibit the inflammatory processes mediated by the chemokine.

Published International Patent Application No. WO 95/19362 describes generically certain dihydropyrrole derivatives as intermediates. Said compounds are disclosed solely as racemates and no reference is made to isomers or isomerism. Furthermore, the only compounds of this type specifically disclosed in WO 95/19362 are unsubstituted in the 5-position of the dihydropyrrole ring.

The synthesis of certain 1,5-dihydro-2H-pyrrol-2-ones is known from: Zh. Org. Khim. (1986) 22: 1749–1756; Zh. Org. Khim (1986) 22: 1790–1791; Khim. Geterotsikl. Soedin. (1987) 5: 625–628; Zh. Org. Khim. (1988) 24: 875–881; Khim.-Farm. Zh. (1991) 25: 37–40; Zh. Org. Khim. (1992) 28: 779–785; *Khim.Geterotsikl. Soedin.* (1992) 1: 32–36; Zh. Obshch. Khim. (1992) 62: 2633–2634; Heterocycles (1993) 36: 2541–2547; *Russian J. Gen Chem.* (1994) 64: 1084–1086; Chem. Heterocycl. Compd. (1998) 34: 739; Russian J. Gen. Chem. (1999) 69: 668–669. The synthesis of certain 3-amino-2-mercaptopyrroles is known from Phos. Sulf. Silic. Relat. Elem. (1999) 148: 117–130.

Compound 1 in the table disclosed hereinafter was purchased from Biospecs in Rijswijk, The Netherlands and compounds 2, 3, 4 and 122 in the table disclosed hereinafter were purchased from Ambinter in Paris, France.

In none of these instances is reference made to pharmaceutical compositions comprising the compounds or to their use as pharmaceuticals.

SUMMARY OF THE INVENTION

The present invention provides pyrrolidinones and pyrrolidine-thiones and analogs thereof which act inter alia as CCR2 antagonists.

The compounds of the invention are indicated for use in treating or preventing conditions in which there is likely to be a component involving MCP-1, CCR2 or the interaction between these two. These conditions include one or more of the following: asthma, seasonal and perennial allergic rhinitis, sinusitus, conjunctivitis, food allergy, scombroid poisoning, psoriasis, urticaria, pruritus, eczema, inflammatory bowel disease, chronic obstructive pulmonary disease, thrombotic disease, otitis media, neuroinflammatory diseases such as multiple sclerosis, atherosclerosis, other inflammatory diseases such as rheumatoid arthritis and nephritis, liver cirrhosis, cardiac disease, pulmonary fibrosis, restenosis such as vascular restenosis, Alzheimer's disease, sepsis, systemic sclerosis, ulcerative colitis, atopic dermatitis, stroke, acute nerve injury, sarcoidosis, hepatitis, endometriosis, HIV infection, AIDS, autoimmune diseases and cancer Accordingly, the invention also provides pharmaceutical compositions comprising the compounds of the invention and methods of treating and/or preventing the diseases set forth above.

The compounds disclosed herein can also be used as research tools to study biological pathways involving both MCP-1 and CCR2.

All patent applications, patents, and other publications recited herein are hereby incorporated by reference in their entirety.

DETAILED DESCRIPTION OF THE INVENTION

In one aspect, the present invention concerns pharmaceutical compositions comprising a compound of formula I

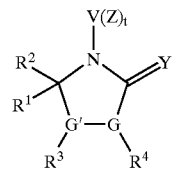

wherein,

Y is oxygen or sulfur;

G and G', together with the bond linking them, are HC—CH or C=C;

V is aryl, heterocycle or cycloalkyl;

Z is halogen, alkyl, alkenyl, alkynyl, hydroxyl, amino, alkoxy, aryloxy, nitro or cyano;

$R^1$ is hydrogen, halogen, alkyl, cycloalkyl, alkenyl, cycloalkenyl, alkynyl, aryl or heterocycle;

$R^2$ is hydrogen or hydroxy;

$R^3$ is —C(O)$R^{3a}$, —C(O)O$R^{3a}$, —C(O)N($R^{3a}$)($R^{3b}$), —S(O)$_2R^{3a}$, —S(O)$R^{3a}$ or —S$R^{3a}$ wherein $R^{3a}$ and $R^{3b}$ have independently the same meaning as $R^1$;

$R^4$ is hydroxy, sulfanyl or amino;

t is 0, 1, 2, 3, 4 or 5;

or a pharmaceutically acceptable salt or metabolically cleavable derivative thereof.

The following paragraphs provide definitions of the various chemical moieties that make up the compounds of the invention and are intended to apply uniformly throughout the specification and claims unless expressly stated otherwise.

The term alkyl as used herein is defined as including a univalent, saturated, straight or branched alkane moiety preferably containing one to ten, especially one to six, carbon atoms and specifically includes, but is not limited to, methyl, ethyl, propyl, isopropyl, butyl, isobutyl, t-butyl, pentyl, isopentyl, neopentyl, hexyl, isohexyl, 3-methylpentyl, 2,2-dimethylbutyl and 2,3-dimethylbutyl.

The term cycloalkyl as used herein is defined as including a mono- or polycyclic alkane moiety preferably containing three to ten carbon atoms and specifically includes, but is not limited to, cyclopropyl, cyclobutyl, cyclopentyl, cyclohexyl, cycloheptyl, cyclooctyl adamantyl and noradamantyl.

The term alkenyl as used herein is defined as including a univalent straight or branched, hydrocarbon with at least one double bond, preferably containing two to ten carbon atoms. Examples include, but are not limited to, vinyl, allyl and 2-butenyl.

The term cycloalkenyl as used herein is defined as including a mono- or polycyclic hydrocarbon with at least one double bond, preferably containing three to ten carbon atoms. Examples include, but are not limited to, 2-cyclohexenyl or bicyclo[2.2.1]hept-5-enyl.

The term alkynyl as used herein is defined as including a univalent straight or branched hydrocarbon with at least one triple bond preferably containing two to ten carbon atoms, and specifically includes, but is not limited to, acetenyl, propynyl, and —C≡C—CH$_2$ (alkyl) including —C≡C—CH$_2$(CH$_3$).

The term aryl as used herein is defined as including phenyl (preferably), biphenyl, napthyl or heteroaryl (as defined below).

The term heterocycle as used herein is defined as including an aromatic moiety that includes at least one heteroatom in the aromatic ring (heteroaryl) as well as a cycloalkyl or cycloalkenyl moiety, as defined above, wherein one or more ring carbon atoms are replaced with a heteroatom. Examples include furyl, pyrryl, pyridyl, pyrimidyl, thienyl, isothiazolyl, imidazolyl, pyrazinyl, benzofuranyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,5-thiadiazolyl, 1,2,4-thiadiazolyl, isooxazolyl, quinazolinyl, pyridazinyl, cinnolinyl, phthalazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, and pyrazolopyrimidinyl as well as pyrrolidinyl, piperidinyl and piperazinyl.

Alkoxy and aryloxy as used herein refer respectively to alkyl or aryl attached to the rest of the molecule via an oxygen atom.

Amino as used herein refers to —$NH_2$ in which one or both of the hydrogen atoms may optionally be replaced by alkyl or aryl or one of each.

Alkyl, alkenyl and alkynyl groups are in the n-form unless otherwise stated and can optionally be substituted with any suitable group including but not limited to one or more, same or different, moieties selected from the group consisting of halo, hydroxyl, nitro, cyano, amino, alkoxy, heterocycle, aryl or aryloxy.

Aryl, cycloalkyl, cycloalkenyl and heterocycle groups can optionally be mono- or poly-(preferably di- or tri-) substituted with any suitable group, including but not limited to one or more, same or different, moieties selected from the group consisting of halogen, alkyl, alkenyl, alkynyl, methylene ($CH_2$=), hydroxyl, amino, alkoxy, aryl, aryloxy, nitro or cyano, whereby when two or more non-cyclic substituents are present these may optionally be linked together to form a ring.

Aryl, cycloalkyl, cycloalkenyl and heterocycle groups may be attached to the pyrrolidine ring either directly or via alkylene (such as in the case of benzyl), alkenylene (such as in the case of styryl) or alkynylene (such as in the case of phenylethynyl).

The term halogen refers to chloro, fluoro, bromo or iodo.

The terms sulfanyl and mercapto each refer to —SH analogously to hydroxy referring to —OH The term heteroatom means O, S, or N.

Where V is substituted by more than one Z moiety these may be the same or different and, when non-cyclic, may optionally be linked together to form a ring.

Unsubstituted valencies are satisfied by hydrogen.

Open valencies on the radical moieties described herein can occur on any one (or more for divalent radicals) of the atoms within the moiety. For example, a monovalent $C_3$ alkyl moiety includes both propyl and isopropyl. As another example, a divalent $C_4$ alkylene moiety includes both tetramethylene (—$CH_2(CH_2)_2CH_2$—), 1,2-dimethylethylene (—$CH(CH_3)$ $(CH_3)CH$—), 1,1-dimethylethylene (—$C(CH_3)_2CH_2$—) and ethylethylene (—$CH(CH_2CH_3)$ $CH_2$—).

"Metabolically cleavable derivatives" are frequently referred to by the term "prodrugs" which refers to compound forms which are rapidly transformed in vivo to the parent compound according to the invention, for example, by hydrolysis in blood. Thus, prodrugs are compounds bearing groups which are removed by biotransformation prior to exhibiting their pharmacological action. Such groups include moieties which are readily cleaved in vivo from the compound bearing it, which compound after cleavage remains or becomes pharmacologically active. Such metabolically cleavable groups form a class well known to practitioners of the art. They include, but are not limited to such groups as alkanoyl (i.e. acetyl, propionyl, butyryl, and the like), unsubstituted and substituted carbocyclic aroyl (such as benzoyl, substituted benzoyl and 1- and 2-naphthoyl), alkoxycarbonyl (such as ethoxycarbonyl), trialklysilyl (such as trimethyl- and triethylsilyl), monoesters formed with dicarboxylic acids (such as succinyl), phosphate, sulfate, sulfonate, sulfonyl, sulfinyl and the like. The compounds bearing the metabolically cleavable groups have the advantage that they may exhibit improved bioavailability as a result of enhanced solubility and/or rate of absorption conferred upon the parent compound by virtue of the presence of the metabolically cleavable group. (T. Higuchi and V. Stella, "Pro-drugs as Novel Delivery System", Vol. 14 of the A.C.S. Symposium Series; "Bioreversible Carriers in Drug Design", ed. Edward B. Roche, American Pharmaceutical Association and Pergamon Press, 1987).

Examples of such compounds include the following:
(5R)-4-acetyl-1-(4-chloro-2-fluorophenyl)-5-cyclohexyl-2-oxo-2,5-dihydro-1H-pyrrol-3-yl ethyl carbonate m.p. 74° C. (compound P1=compound no. 125 in which hydroxy is replaced by ethoxycarbonyloxy);
4-acetyl-5-cyclohexyl-1-(4-methylphenyl)-2-oxo-2,5-dihydro-1H-pyrrol-3-yl benzoate (MS 418) (compound P2=compound no. 10 in which hydroxy is replaced by benzoyloxy).

As used herein, the term "pharmaceutically acceptable salts" refers to salts that retain the desired biological activity of the above-identified compounds and exhibit minimal or no undesired toxicological effects. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as citric acid, acetic acid, oxalic acid, tartaric acid, succinic acid, malic acid, fumaric acid, ascorbic acid, benzoic acid, tannic acid, palmoic acid, alginic acid, polyglutamic acid, napthalenesulfonic acid, napthalenedisulfonic, and polygalacturonic acid as well as base addition salts such as those formed with alkali- and alkaline earth metals such as sodium, potassium and calcium The compounds can also be administered as pharmaceutically acceptable quaternary salts known by those skilled in the art, which specifically include, but not limiting to the quaternary ammonium salt of the formula —$NR^+Z^-$, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as fumarate, benzoate, succinate, acetate, glycolate, maleate, malate, fumarate, citrate, tartrate, ascorbate, benzoate, cinnamoate, mandeloate, benzyloate, and diphenylacetate).

In accordance with the invention all stereoisomeric forms such as enantiomeric and diastereoisomeric forms of the compounds of formula I or mixtures thereof (including all possible mixtures of stereoisomers and racemates) are included. Typically one of the enantiomeric forms (eutomer) will be more therapeutically attractive than the other (distomer). In the case of the compounds according to the invention it is the (–)-form which is the eutomer and thus preferred. In compounds where the carbon atom at position 5 in the pyrrolidinone or pyrrolidine-thione ring is assymetric it is typically the "R" enantiomer which is preferred. X-Ray analysis has confirmed that in the present case the "R" and "–" enantiomers correspond.

Furthermore certain compounds of formula I which contain alkenyl groups may exist as Z (zusammen) or E (entgegen) isomers. In each instance, the invention includes both mixture and separate individual isomers.

Multiple substituents on the scaffold ring can also stand in either cis or trans relationship to each other with respect to the plane of the ring. In each instance, the invention includes both mixture and separate individual forms.

Some of the compounds of formula I may also exist in tautomeric forms. Such forms although not explicity indicated in the above formula are intended to be included within the scope of the present invention.

With respect to the present invention reference to a compound is intended to encompass that compound in each of its possible forms including geometrical isomers, enantiomers, diastereomers, and mixtures thereof (racemates) unless the particular isomeric form is referred to specifically.

The substituents the compounds of formula I preferably have the following meanings:

for Y, oxygen;
for G and G', together with the bond linking them, C=C;
for V,
   a) aryl, especially phenyl, benzyl, naphthyl, naphthylmethyl, indenyl, dihydro indenyl; heterocycle especially pyridyl;
   b) phenyl, benzyl or dihydroindenyl;
   c) phenyl or dihydroindenyl;
   d) phenyl or benzyl;
   e) phenyl;
for Z,
   a) halogen, alkyl, alkoxy, OH, $NO_2$ or $NH_2$;
   b) halogen, alkyl, alkoxy, $NO_2$ or $NH_2$;
   c) fluoro, chloro, bromo, iodo, $C_{1-4}$-alkyl, $C_{1-4}$alkoxy, especially methoxy, trifluoromethyl, $NO_2$ or $NH_2$;
   d) fluoro, chloro, bromo, $C_{1-4}$-alkyl, $C_{1-4}$ alkoxy, especially methoxy, trifluoromethyl, $NO_2$ or $NH_2$;
   e) fluoro, chloro, bromo, iodo, $C_{1-4}$ alkyl especially methyl or ethyl;
   f) fluoro, chloro, bromo, $C_{1-4}$ alkyl especially methyl or ethyl;
for t, 0, 1, 2 or 3 especially 0, 1 or 2;
for $R^1$,
   a) alkyl, in particular $C_{1-10}$, especially $C_{1-8}$ alkyl, cycloalkyl, especially $C_{3-10}$ cycloalkyl, cycloalkenyl, especially $C_{6-8}$ cycloalkenyl, phenyl or heterocycle;
   b) $C_{1-8}$ alkyl, especially, methyl, ethyl, propyl, i-propyl, 3,3,3-trifluoropropyl, i-butyl, t-butyl, pentyl, 1-ethylpropyl, neo-pentyl, 1,2-dimethylbutyl or 1-propylbutyl particularly 1-ethylpropyl, $C_{3-10}$ cycloalkyl especially cyclopropyl, cyclopentyl, cyclohexyl, cyclohexylmethyl, cycloheptyl, cyclooctyl, adamantyl or noradamantyl, particularly cyclopentyl or cyclohexyl, notably cyclohexyl, $C_{6-8}$ cycloalkenyl especially 2-cyclohexenyl or bicyclo [2.2.1]hept-5-enyl, particularly the latter, furyl, thienyl or phenyl, optionally substituted by one or more alkyl, especially methyl, halogen, especially fluoro, chloro or bromo or cyano;
for $R^2$, hydrogen;
for $R^3$, —C(O)$R^{3a}$ wherein $R^{3a}$ is alkyl, aryl or heterocycle, especially preferred as $R^{3a}$ are $C_{1-5}$-alkyl, phenyl, benzyl, phenethyl, or thienyl with methyl being most preferred;
for $R^4$, hydroxy.

Combinations of the above preferred substituent meanings are especially preferred.

Particularly preferred compounds of formula I are those wherein Y is oxygen, $R^4$ is hydroxy, G and G', together with the bond linking them, are C=C and the remaining substituents are as variously defined above and pharmaceutically acceptable salts thereof (compounds IA).

Within compounds IA those compounds are particularly preferred wherein $R^3$ is acetyl and $R^2$ is hydrogen and pharmaceutically acceptable salts thereof (compounds IB).

Preferred individual compounds are nos. 10, 13, 17, 18, 24, 25, 51, 53, 54, 56, 63, 65, 69, 70, 72, 79, 118, 119, 120, 121, 125, 127, 129, 135, 137, 139, 140, 141, 142, 144, 148, 149, 150, 151, 153, 154, 155, 156, 157 and 169 as hereinafter described whereby compounds 10, 17, 18, 24, 51, 53, 54, 69, 72, 118, 119, 120, 121, 125, 127, 129, 135, 137, 139, 140, 141, 142, 144, 148, 149, 150, 151, 153, 154, 155, 156, 157 and 169 are especially preferred, with 51, 125, 129, 140, 144, 148, 149, 155 and 156 being most preferred.

Within the compounds of formula I certain compounds are novel and may be defined as follows with respect to the individual substituent meanings:

for Y, sulfur (compounds IIA);
for $R^1$ and $R^2$,
   a) $R^1$ is hydrogen, halogen, alkyl, cycloalkyl, alkenyl, cycloalkenyl, alkynyl, aryl or heterocycle and $R^2$ is hydroxy (compounds IIB); or
   b) $R^1$ is as defined above except for hydrogen, $C_{1-7}$-alkyl, phenyl, $C_{3-5}$-cycloalkyl, or methylene ($C_{3-5}$-cycloalkyl) wherein each alkyl or phenyl group may be substituted with one or two methyl, methoxy, ethyl or trifluoromethyl, or up to three halogens and $R^2$ is hydrogen (compounds IIC);
   c) one of $R^1$ and $R^2$ is other than hydrogen (compounds IID);

for $R^3$, as defined above except for —C(O)$R^{3c}$ wherein $R^{3c}$ is hydrogen, $C_{1-7}$-alkyl, $C_{2-3}$-alkenyl, phenyl, $C_{3-5}$-cycloalkyl, or methylene ($C_{3-5}$-cycloalkyl) wherein each alkyl, phenyl or alkenyl group may be substituted with one nitro, methoxy or ethoxy, with one or two methyl, ethyl or trifluoromethyl, or with up to three halogens (compounds IIE);

and, in each case the remaining substituents are as defined above.

Compounds of formula I in fully or partially resolved isomeric form (compounds IIF) are also novel as are all individual compounds in the table set forth hereinafter with the exception of compounds nos. 1, 2, 3, 4, 5, 9 and 122 (compounds IIG).

The novel compound groups IIA to IIG also form part of the invention

The present invention concerns also a process for preparing the compounds having general formula I.

The synthetic scheme set forth below illustrates how compounds according to the invention can be made. Those skilled in the art will be able to routinely modify and/or adapt the following scheme to synthesize any compound of the invention covered by formula I.

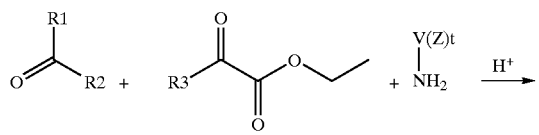

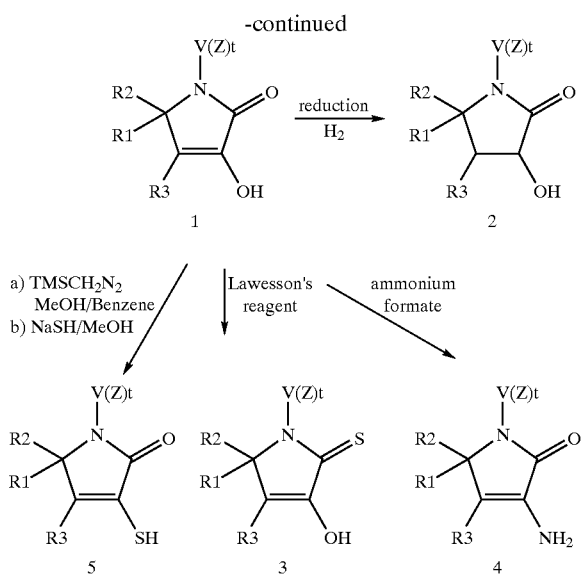

Compounds of formula 1 may be obtained by the condensation of an amine of formula $V(Z)_t$—$NH_2$ and two carbonylic compounds of formulae $R^1C(O)R^2$ and $R^3C(O)C(O)OEt$ in acidic conditions.

Several analogues can be obtained from compound 1. For example compound 2 can be obtained by reduction of compound 1 with a suitable reducing agent. The carbonylic group in position 2 can be converted to the corresponding thio group after submission to Lawesson's reagent (phosphorus pentasulfide). The enolic function can be converted to the corresponding amine after reaction in the presence of ammonium formate. Compound 5 can be prepared by conversion of compound 1 to the corresponding methoxy compound in the presence of trimethylsilyldiazomethane and then convertion to the sulfanyl analog in the presence of sodium hydrosulfide.

As will be evident to those skilled in the art, individual isomeric forms can be obtained by separation of mixtures thereof in conventional manner.

For example, in the case of geometric isomers, chromatographic separation may be employed.

For separation of individual optical isomers from racemic forms for example the racemic mixture of an enolic parent compound can be derivatised and resolved by SMB (simulated moving bed) chromatography and then cleaved back to the single enantiomers at the enol function.

Alternatively separation can be achieved by fractional crystalisation of diastereomeric salts.

Utility

As mentioned above, the compounds of the invention possess CCR2 antagonist activity and are therefore indicated for use in treating a variety of conditions in which there is likely to be a component involving MCP-1, CCR2 or the interaction between these two such as asthma, seasonal and perennial allergic rhinitis, sinusitus, conjunctivitis, food allergy, scombroid poisoning, psoriasis, urticaria, pruritus, eczema, inflammatory bowel disease, chronic obstructive pulmonary disease, thrombotic disease, otitis media, neuroinflammatory diseases such as multiple sclerosis, atherosclerosis, other inflammatory diseases such as rheumatoid arthritis and nephritis, liver cirrhosis, cardiac disease, pulmonary fibrosis, restenosis such as vascular restenosis, Alzheimer's disease, sepsis, systemic sclerosis, ulcerative colitis, atopic dermatitis, stroke, acute nerve injury, sarcoidosis, hepatitis, endometriosis, HIV infection, AIDS, autoimmune disease and cancer.

In addition certain compounds of the invention exhibit cross reactivity with other chemokine receptors especially CCR1 and CCR5.

As described below, several disease models have been used to demonstrate the efficacy of inhibiting the interaction between MCP-1 and CCR2. In addition, clinical studies have provided evidence of the strong correlation between MCP-1 and CCR2 expression and the incidence and severity of human diseases.

Several studies have linked CCR2 with the pathogenesis of asthma. In mouse models of lung inflammation and hyperreactivity, inhibition of MCP-1 with a monoclonal antibody significantly decreases allergen-induced infiltration of leukocytes into the lung and also decreases airway hyperreactivity (Lukacs, N. et al (1997) *J. Immunol.* 158: 4398; Gonzalo, J. et al (1998), *J. Exp. Med.* 188: 157). The effect of blocking MCP-1 was greater than that of blocking other chemokines, such as eotaxin, MIP-1α, and RANTES. In CCR2 knockout mice, allergen-induced hyperreactivity was also decreased, as was the release of histamine into the lung (Campbell, E. et al (1999), *Immunol.* 163: 2160). In human studies, it has been shown that MCP-1 in both bronchoalveolar lavage and bronchial tissue is significantly increased in asthmatics (Sousa, A. et al (1994), *Am. J. Respir. Cell Mol. Biol.* 10: 142; Alam, R. et al (1996), *Am. J. Respir. Crit. Care Med.* 153: 1398; Holgate, S. et al (1997), *A. J. Respir. Crit. Care Med.* 156: 1377). In addition, levels of MCP-1 are correlated with the incidence of attacks and the severity of symptoms (Sousa, A. et al (1994), *Am. J. Respir. Cell Mol. Biol.* 10: 142; Alam, R. et al (1996), *Am. J. Respir. Crit. Care Med.* 153: 1398; Holgate, S. et al (1997), *A. J. Respir. Crit. Care Med.* 156: 1377; Lummus, Z. et al (1998), *J. Allergy Clin. Immunol.* 102: 265; Jahnz-Rozyk, K. et al (1997), *Immunol. Lett.* 58: 47). Asthmatic patients who respond positively to immunotherapy also show a reduction in plasma levels of MCP-1. (Hsieh, K. et al (1996), *J. Allergy Clin Immunol.* 98: 580).

MCP-1 has also been shown to be elevated in the lung tissues and secretions of patients with other respiratory diseases such as chronic obstructive pulmonary disease (COPD)(Capelli, A. et al (1999), *Eur. Resp. J.* 14: 160; de Boer, W. et al (2000), *J. Pathol.* 190: 619), allergic rhinitis (Kimura et al (1998), *Lab. Invest.* 78:571; Fujikura et al (2001), *J. Allergy Clin. Immunol* 107:123), and pulmonary fibrosis (Antoniades, H. et al (1992), *Proc. Nat. Acad. Sci.* 89:5371; Iyonaga, K. et al (1994), *Hum. Pathol.* 25:455; Hasegawa, M. et al (1999), *Clin Exp. Immunol.* 117:159). In an animal model of pulmonary fibrosis using CCR2-deficient (knockout) mice, it was shown that lung damage was significantly decreased in the knockout mice (Moore et al (2001), *J. Immunol.* 167:4368).

Several studies have demonstrated an association of MCP-1 and CCR2 with the neuroinflammatory disease multiple sclerosis (MS). Experimental autoimmune encephalomyelitis (EAE), which is an animal model of MS, is initiated by an autoimmune T cell response to myelin followed by infiltration of macrophages into the CNS which brings about demyelination and paralysis. Studies with the EAE model have shown MCP-1 levels in the CNS of mice to be correlated with the severity of relapses (Kennedy, K. et al (1998), *J. Neuroimmunol.* 92: 98). In addition, treatment with an anti-MCP-1 antibody reduced the clinical severity of the relapsing disease. Knockout mice lacking either MCP-1 (Huang, D. et al (2001), *J. Exp. Med.* 193: 713) or CCR2 (Fife, B. et al (2000), *J. Exp. Med.* 192: 899; Izikson, L. et al (2000), *J. Exp. Med.* 192: 1075) show a significantly increased resistance to EAE compared to wildtype mice. In studies with post-mortem human brain tissue, it has been demonstrated that MCP-1 is elevated in demyelinating MS lesions (Simpson, J. et al (1998), *J. Neuroimmunol.* 84: 238; Van der Voorn, P. et al (1999), *Am. J. Path.* 154: 45).

Atherosclerosis is a disease whereby hypercholesterolemia induces an influx of monocytes into the subendothelium, which subsequently differentiate into foam cells which grow into atherosclerotic plaques. Studies in animals and humans have shown MCP-1 to be involved in the pathogenesis of this disease. In hypercholesterolemic (Apo E deficient) mice, the expression of both MCP-1 and CCR2 is elevated in atherosclerotic lesions (Rayner, K. et al (2000), *J. Vasc. Res.* 37: 93). Overexpression of MCP-1 in transgenic mice results in an increase in the incidence of atherosclerosis in animals (Aiello, R. et al (1999), *Arterioscler. Thromb. Vasc. Biol.* 19: 1518). Knockout mice which lack either MCP-1 (Gu, L. et al (1998), *Mol. Cell* 2: 275; Gosling, J. et al (1999), *J. Clin. Invest.* 103: 773) or CCR2 (Boring, L. et al (1998), *Nature* 394: 894; Dawson, T. et al (1999), *Atherosclerosis* 143: 205) show a significant reduction in atherosclerotic lesions. In humans, it has been shown that CCR2 expression in blood monocytes is increased in hypercholesterolemic patients and that this correlates with increased responsiveness to MCP-1 (Han, K. et al (1999), *J. Lipid Res.* 40: 1053).

Plasma levels of MCP-1 have been shown to increase significantly in patients after angioplasty and has been correlated with the incidence of vascular restenosis (Hokimoto et al (2000), *Japan Circ. J.* 64:831; Cipollone et al (2000), *Arter. Throm. Vasc. Biol.* 21:327; Economou et al (2001), *Int. J. Cardiol.* 80:55). Similar results have been observed after stent implantation (Oshima et al (2001) *Japan Circ. J.* 65:261). Studies with blocking anti-MCP-1 antibodies have shown decreased incidence and severity of neointimal thickening in animal models (Furukawa et al (1999), *Circ. Res.* 84:306; Koyanagi et al (2000), *Circulation* 102:2243). Decreased neointimal hyperplasia has also been demonstrated in a CCR2 knockout mouse model (Egashira et al (2002), *Circ. Res.* 90:1167).

Studies have linked MCP-1 to two other inflammatory diseases, rheumatoid arthritis (RA) and nephritis. In animal models of arthritis, a neutralizing anti-MCP-1 antibody (Ogata, H. et al (1997), *J. Pathol.* 182: 106) and a mutated MCP-1 peptide antagonist to CCR2 (Gong, J. et al (1997), *J. Exp. Med.* 186: 131) were both found to inhibit disease. Human studies have shown MCP-1 to be elevated in both the blood and synovial fluid from RA patients (Benedetti, F. et al (1999), *J. Rheumatol.* 26: 425; Ross, E. et al (2000), *J. Rheumatol.* 27: 2432; Ellingsen, T. et al (2001), *J. Rheumatol.* 28: 41). Levels of MCP-1 in the synovium correlates with severity of the disease. Animal models of glomerulonephritis have demonstrated that MCP-1 is elevated during the disease, and this is correlated with increased macrophage infiltration into the kidney as well as proteinuria. Several experiments have shown that blocking MCP-1 with antibody results in decreased severity of the disease (Tang, W. et al (1996), *Kidney Int.* 50: 665; Wada, T. et al (1996), *FASEB J.* 10: 1418; Fujinaka, H. et al (1997), *J. Am. Soc. Nephrol.* 8: 1174; Lloyd, C. et al (1997), *J. Exp. Med.* 185: 1371). MCP-1 knockout mice also show a reduction in tubular injury (Tesch, G. et al (1999), *J. Clin. Invest.* 103: 73). In human nephropathies, MCP-1 is elevated in the kidney and the urine, and levels of the chemokine are correlated with disease activity (Yokoyama, H. et al (1998), *J. Leuk. Biol.* 63: 493; Saitoh, A. et al (1998), *J. Clin. Lab. Anal.* 12: 1).

Several additional studies in both animals and humans have demonstrated the association of MCP-1 with various other diseases. These include stroke (Haro et al (1996), *Spine* 21:1647; Umehara et al (1996), *Acta Neuropathol.* 91:343), skin diseases such as atopic dermatitis (Kaburagi, Y. et al (2000), *Arch. Dermatol. Res.* 293:350) and psoriasis (Deleuran, M. et al (1996), *J. Dermatol. Sci.* 13: 228), liver cirrhosis (Marra, F. et al (1998), *Am. J. Pathol.* 152: 423; Fisher, N. et al (1999), *Gut* 45: 416; Tsuneyama, K. et al (2001), *J. Pathol.* 193: 102), alcoholic hepatitis (Fisher, N. et al (1999), *Gut* 45:416), sarcoidosis (Hashimoto, S. et al (1998), *Clin. Exp. Immunol.* 111: 604; Iyonaga, K. et al (1998), *Sarcoidosis Vasc. Diffuse Lung Dis.* 15: 165), cardiac diseases (Nishiyama, K. et al (1998), *Jpn. Circ. J.* 62: 710; Ono, K. et al (1999), *Lab. Invest.* 79: 195; Damas, J. et al (2000), *Cardiovasc. Res.* 47: 778), sepsis (Hogaboam, C. et al (1998), *Infect. Immun.* 66: 650; Neumann, B. et al (1999), *Int. Immunol.* 11: 217), Alzheimer's disease (Grammas et al (2001), *Neurobiol. Aging* 22:837), systemic sclerosis (Hasegawa, M. et al (1999), *Clin. Exp. Immunol.* 117: 159) inflammatory bowel diseases such as ulcerative colitis (Ugoccioni, M. et al (1999), *Am. J. Pathol.* 155: 331) and Crohn's disease (McCormack, G. et al (2001), *Inflamm. Res.* 50:491), and endometriosis (Akoum et al (1996), *Fertil. Steril.* 66:17). Numerous studies with neutralizing antiMCP-1 antibodies have shown improvements in disease symptoms in animal models of myocardial infarction (Ono, K. et al (1999), *Lab. Invest.* 79: 195), stroke (Galasso et al (2000), *Neuroscience* 101:737), dermatitis (Gordon, J. et al (2000), *J. Allergy Clin. Immunol.* 106:110) and sarcoidosis (Ichiyasu et al (2001), *Microsc. Res. Tech.* 53:288).

Treatment or prevention can be carried out by administering to the patient an effective amount of one or more compounds according to the invention in a pharmaceutically acceptable carrier or diluent. The active materials can be administered by any appropriate route, for example, orally, parenterally, intravenously, intradermally, subcutaneously, intramuscularly or topically, in liquid, cream, gel or solid form, via a buccal or nasal spray, or aerosol.

The active compound is included in the pharmaceutically acceptable carrier or diluent in an amount sufficient to deliver to a patient a therapeutically effective amount without causing serious toxic effects in the patient treated. A preferred dose of the active compound for all of the above-mentioned conditions is in the range from about 0.01 to 300 mg/kg, preferably 0.1 to 100 mg/kg per day, more generally 0.5 to about 25 mg per kilogram body weight of the recipient per day. A typical topical dosage will range from 0.01–3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

The methods of the invention comprise administration to a mammal (preferably human) suffering from a MCP-1 or CCR2 mediated condition (preferably, asthma or rhinitis) a pharmaceutical composition according to the invention in an amount sufficient to alleviate the condition. The compound is conveniently administered in any suitable unit dosage form, including but not limited to one containing 1 to 3000 mg, preferably 5 to 500 mg of active ingredient per unit dosage form. An oral dosage of 1–500, preferably 10–250, more preferably 25–250 mg is usually convenient.

The active ingredient should be administered to achieve peak plasma concentrations of the active compound of about 0.001–30 μM, preferably about 0.01–10 μM. This may be achieved, for example, by the intravenous injection of a solution or formulation of the active ingredient, optionally in saline, or an aqueous medium or administered as a bolus of the active ingredient.

The concentration of active compound in the drug composition will depend on absorption, distribution inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterores; a lidant such as colloidal silicon dioxide; a sweetening agent such as sucrose or saccharine; or a flavoring agent such as peppermint, methyl salicylate, or orange flavoring. When the dosage unit form is a capsule, it can contain in addition to material of the above type, a liquid carrier such as fatty oil. In addition, dosage unit forms can contain various other materials which modify the physical form of the dosage unit, for example, coatings of sugar, shellac, or enteric agents.

The active compound or pharmaceutically acceptable salt or derivative thereof can be administered as a component of an elixir, suspension, syrup, wafer, chewing gum or the like. A syrup may contain, in addition to the active compounds, sucrose as a sweetening agent and certain preservatives, dyes and colorings and flavors.

Other components used in oral or topical compositions include emulsifying agents or penetration enhancers such as oleic acid and stabilising or solubilising agents such as cyclodextrins.

Solutions or suspensions used for parenteral, intradermal, subcutaneous, or topical application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation (CA) and Guilford Pharmaceuticals (Baltimore, Md.). Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidylcholine, arachadoyl phosphatidylcholine and cholesterol) in an organic solvent that is then evaporated, leaving behind a thin film of dried lipid on the surface of the container. An aqueous solution of the active compound or its monophosphate, diphosphate, and/or triphosphate derivatives are then introduced into the container. The container is then swirled by hand to free lipid material from the sides of the container and to disperse lipid aggregates, thereby forming the liposomal suspension.

The active compound or pharmaceutically acceptable salt or derivative thereof can also be mixed with other active materials that do not impair the desired action, or with materials that supplement the desired action, such as adrenergic agonists like pseudoephedrine, antibiotics, antifungals, other anti-inflammatories, or antiviral compounds.

The present invention concerns also a method of treating or preventing conditions mediated by CCR2, MCP-1 or the interaction thereof, the method comprising administering to a patient an amount of a compound having the formula I or a pharmaceutically active derivative or salt thereof sufficient to prevent, reduce or eliminate the condition.

The method is particularly useful in the treatment or prevention of a condition selected from asthma, seasonal and perennial allergic rhinitis, sinusitus, conjunctivitis, food allergy, scombroid poisoning, psoriasis, urticaria, pruritus, eczema, inflammatory bowel disease, chronic obstructive pulmonary disease, thrombotic disease, otitis media, neuroinflammatory diseases such as multiple sclerosis, atherosclerosis, other inflammatory diseases such as rheumatoid arthritis and nephritis, liver cirrhosis, cardiac disease, pulmonary fibrosis, restenosis such as vascular restenosis, Alzheimer's disease, sepsis, systemic sclerosis ulcerative colitis, atopic dermatitis, stroke, acute nerve injury, sarcoidosis, hepatitis, endometriosis, HIV infection, AIDS, autoimmune diseases and cancer.

The method is particularly useful in the treatment or prevention of asthma, atherosclerosis, multiple sclerosis and rheumatoid arthritis.

The present invention concerns also the use of a compound having general formula I, or a pharmaceutically active derivative or salt thereof for the manufacture of a medicament for a therapeutic application.

The present invention concerns also a method for manufacturing a medicament intended for therapeutic application, wherein a compound having general formula I or a pharmaceutically active derivative or salt thereof is used.

The following Examples are provided for illustrative purposes only and are not intended, nor should they be construed, as limiting the invention by any other manner. Those skilled in the art will appreciate that routine variations and modifications of the following Examples can be made without exceeding the scope of the invention.

EXAMPLE 1

Preparation of 4-acetyl-5-cyclohexyl-3-hydroxy-1-(4-methylphenyl)-1,5-dihydro-2H-pyrrol-2-one (Compound 10)

To a stirring solution of p-toluidine (430 mg, 4.0 mmol) in 4 ml of acetic acid at room temperature, are added cyclohexane carboxaldehyde (450 mg, 4.0 mmol) and ethyl acetopyruvate (640 mg, 4.0 mmol). The reaction mixture is heated to 95° C., stirred for 120 minutes, cooled to room temperature and the solvent removed under reduced pressure. Diethyl ether (10 ml) is added to the residue and the mixture stirred for 30 minutes whereupon a white precipitate forms. The final compound is collected after filtration as a white crystalline solid mp 222° C. The filtrate may be concentrated to give additional compound.

$^1$H NMR (300 MHz, CDCl$_3$): δ0.80–1.20 (m, 5H), δ1.40–1.79 (m, 5H), δ1.96 (m, 1H), δ2.41 (s, 3H), δ2.56 (s, 3H), 4.97 (d, 1H, J=0.9 Hz), 7.29 (m, 4H), 8.90 (s, br, 1H) ppm.

The racemic mixture can be resolved on a chiral HPLC column (Chiral Cel OD-H) using a mixture of isopropyl alcohol (15)/hexanes (85) and 0.1% TFA, flow rate 0.5 ml/min, or it can be resolved by using a chiral auxiliary.

EXAMPLE 2

Preparation of 1-(4-chlorophenyl)-5-cyclohexyl-3-hydroxy-4-[3-(4-hydroxyphenyl)propanoyl]-1,5-dihydro-2H-pyrrol-2-one (Compound 67)

To a stirring solution of 4-hydroxy benzyl acetone in 40 mL of dry DMF at room temperature, are added 0.96 g (40 mmol) of sodium hydride. The reaction mixture turns deep yellow and after 30 minutes diethyl oxalate (5.43 mL, 40 mmol) is added. The mixture is stirred overnight at room temperature, then quenched with HCl 10% and extracted with ethyl acetate. The organic layers are washed with water, dried over magnesium sulfate, filtered and the solvent is evaporated under reduced pressure. The formation of the desired ethyl 6-(4-hydroxyphenyl)-2,4-dioxohexanoate is checked by H$^1$-NMR before being used further without purification.

To a stirring solution of p-chloraniline (320 mg, 2.5 mmol) in 2.5 mL of acetic acid at room temperature, are added cyclohexane carboxaldehyde (0.30 mL, 2.5 mmol) and ethyl 6-(4-hydroxyphenyl)-2,4-dioxohexanoate (618 mg, 2.5 mmol). The reaction mixture is stirred at room temperature. After 30 minutes a white precipitate is formed. The solvent is removed under reduced pressure and the crude material recrystallized from a mixture of ether/methanol. The final compound is collected after filtration as a white crystalline solid m.p. 259° C.

$^1$H NMR (300 MHz, DMSO-d$_6$): δ0.80–1.20 (m, 5H), δ1.40–1.79 (m, 5H), δ2.80 (t, 2H), δ3.0–3.2 (m, 2H), δ5.05 (s, 1H), δ6.65 (d, 2H), δ7.0 (d, 2H), δ7.55 (q, 2H), δ9.17 (s,1H), δ12.1 (s, br, 1H) ppm.

EXAMPLE 3

Preparation of 4-acetyl-5-cyclohexyl-3-amino-1-(4-methylphenyl)-1,5-dihydro-2H-pyrrol-2-one (Compound 61)

A reaction mixture of 4-acetyl-5-cyclohexyl-3-hydroxy-1-(4-methylphenyl)-1,5-dihydro-2H-pyrrol-2-one (139 mg, 0.44 mmol) and ammonium formate (342 mg, 4.44 mmol) in ethanol (0.2M, 2.2 ml) is heated at reflux for 16 hours. The solvent is removed in vacuo to give a white residue. Water is added to the residue to dissolve some of the white solid leaving a sandy-coloured precipitate. This mixture is then filtered, washed with a small amount of diethyl ether and dried under high vacuum at room temperature to give a pale brown solid.

$^1$H NMR (400 MHz, CDCl$_3$): δ10.07 (s, br, 1H), 7.36 (d, 2H), 7.22 (d,2H), 6.41 (s, br, 1H), 4.83 (d, 1H), 2.36 (s, 3H), 2.19 (s, 3H), 1.80–0.96 (m, 9H).

EXAMPLE 4

Preparation and Enantiomeric Resolution of 4-acetyl-1-(4-chloro-2-fluorophenyl)-5-cyclohexyl-3-hydroxy-1,5-dihydro-2H-pyrrol-2-one A. Preparation of 4-acetyl-1-(4-chloro-2-fluorophenyl)-5-cyclohexyl-3-hydroxy-1,5-dihydro-2H-pyrrol-2-one (compound 72).

To a stirred solution of 4-chloro-2-fluoroaniline (727 mg, 5.0 mmol) in THF (10 ml) at room temperature is added dropwise cyclohexanecarboxaldehyde (0.6 ml, 5.0 mmol). The reaction mixture is stirred for 12 hours at room temperature. Then, ethyl 2,4-dioxovalerate (0.7 ml, 5.0 mmol) is added dropwise at room temperature and the reaction is stirred for another 12 hours. The solvent is removed under reduced pressure and the black residue is dissolved in acetonitrile. The mixture is stirred for 15 minutes, filtered and dried under high vacuum to yield the product as a white solid (220 mg).

$^1$H NMR (CDCl$_3$) δ0.63 (dq, 1H), 0.82–1.18 (m, 4H), 1.42–1.78 (m, 5H), 1.93 (tq, 1H), 2.51 (s, 3H), 4.96 (d, 1H), 7.23–7.26 (m, 2H), 7.36 (dt, 1H). IR (NaCl) 3151, 2929, 1689, 1643, 1501, 1220. MS (ES+) 352.1 (M$^+$).

B. Preparation of methyl (2R)-{[4-acetyl-1-(4-chlorophenyl)-5-cyclohexyl-2-oxo-2,5-dihydro-1H-pyrrol-3-yl]oxy}(phenyl)ethanoate To a cooled (0° C.) mixture of 4-acetyl-1-(4-chloro-2-fluorophenyl)-5-cyclohexyl-3-hydroxy-1,5-dihydro-2H-pyrrol-2-one (2.05 g, 5.84 mmol), methyl (S)-mandelate (1.36 g, 8.18 mmol) and triphenylphosphine (2.0 g, 7.6 mmol) in THF (50 ml) is added dropwise DIAD (1.6 ml, 7.6 mmol). The reaction is then left to warm to room temperature and is stirred for 12 hours. The solvent is removed under vacuum and the oily residue is plugged through a pad of silica gel (eluent 1/1 hexanes/ethyl acetate). The solvent is removed and the residual oil is purified by radial chromatography (eluent 9/1 hexanes/ethyl acetate) to yield each diastereomer (1 g) as a white foam.

C. Preparation of (5R)-4-acetyl-1-(4-chloro-2-fluorophenyl)-5-cyclohexyl-3-hydroxy-1,5-dihydro-2H-pyrrol-2-one (Compound 125).

To a stirred solution of methyl (2R)-{[4-acetyl-1-(4-chlorophenyl)-(5R)-cyclohexyl-2-oxo-2,5-dihydro-1H-pyrrol-3-yl]oxy}(phenyl)ethanoate (diastereomer eluting first) (1.0 g, 2.0 mmol) in 1,4-dioxane (20 ml) is added by portions 10% Pd/C (300 mg). The reaction vessel is flushed with hydrogen and a balloon filled with H$_2$ is fitted to the flask. The reaction is monitored by thin layer chromatography. Upon completion, the reaction mixture is filtered through cotton and the solvent is removed under vacuum. The residue is purified by reverse-phase chromatography (acetonitrile/water 20%ACN to 100% ACN over 8 mns). The solvent is removed under high vacuum to yield the product as a white foam (364 mg).

$^1$H NMR (CDCl$_3$) δ0.63 (dq, 1H), 0.82–1.18 (m, 4H), 1.42–1.78 (m, 5H), 1.93 (tq, 1H), 2.51 (s, 3H), 4.96 (d, 1H), 7.23–7.26 (m, 2H), 7.36 (dt, 1H). IR (NaCl) 3151, 2929, 1689, 1643, 1501, 1220. MS (ES+) 352.1 (M$^+$)."

The following compounds may be prepared analogously. As used herein RACEMATE refers to a mixture of all enantiomers, MIXTURE refers to a mixture of diastereoisomers and CHIRAL refers to a pure enantiomer.

TABLE 1

| Cpd. No. | Name | stereochemistry | melting point in ° C. or (mass spec) |
|---|---|---|---|
| 1 | 4-acetyl-1-benzyl-5-(4-bromophenyl)-3-hydroxy-1,5-dihydro-2H-pyrrol-2-one | RACEMATE | 207 |
| 2 | 4-acetyl-5-(4-bromophenyl)-1-(5-bromopyridin-2-yl)-3-hydroxy-1,5-dihydro-2H-pyrrol-2-one | RACEMATE | 258 |
| 3 | 4-acetyl-1-benzyl-5-(2-fluorophenyl)-3-hydroxy-1,5-dihydro-2H-pyrrol-2-one | RACEMATE | 234 |
| 4 | 4-acetyl-1-benzyl-5-(4-chlorophenyl)-3-hydroxy-1,5-dihydro-2H-pyrrol-2-one | RACEMATE | 262 |
| 5 | 4-acetyl-1-benzyl-3-hydroxy-5-phenyl-1,5-dihydro-2H-pyrrol-2-one | RACEMATE | 188 |
| 6 | 4-acetyl-1-benzyl-5-(4-fluorophenyl)-3-hydroxy-1,5-dihydro-2H-pyrrol-2-one | RACEMATE | (326) |
| 7 | 4-acetyl-1-benzyl-5-cyclohexyl-3-hydroxy-1,5-dihydro-2H-pyrrol-2-one | RACEMATE | (314) |
| 8 | 4-acetyl-1-benzyl-5-(2-furyl)-3-hydroxy-1,5-dihydro-2H-pyrrol-2-one | RACEMATE | 174 |
| 9 | 4-acetyl-1,5-bis(4-bromophenyl)-3-hydroxy-1,5-dihydro-2H-pyrrol-2-one | RACEMATE | 132 |
| 10 | 4-acetyl-5-cyclohexyl-3-hydroxy-1-(4-methylphenyl)-1,5-dihydro-2H-pyrrol-2-one | RACEMATE | 222 |
| 11 | 4-acetyl-3-hydroxy-5-isopropyl-1-(4-methylphenyl)-1,5-dihydro-2H-pyrrol-2-one | RACEMATE | (274) |
| 12 | 4-acetyl-5-tert-butyl-3-hydroxy-1-(4-methylphenyl)-1,5-dihydro-2H-pyrrol-2-one | RACEMATE | 189 |
| 13 | 4-acetyl-5-(1-ethylpropyl)-3-hydroxy-1-(4-methylphenyl)-1,5-dihydro-2H-pyrrol-2-one | RACEMATE | 146 |
| 14 | 4-acetyl-5-cyclohexyl-3-hydroxy-1-(4-methoxyphenyl)-1,5-dihydro-2H-pyrrol-2-one | RACEMATE | 194 |
| 15 | 4-acetyl-5-(4-chlorophenyl)-3-hydroxy-1-(4-methylphenyl)-1,5-dihydro-2H-pyrrol-2-one | RACEMATE | 197 |
| 16 | 4-acetyl-5-cyclohexyl-3-hydroxy-1-(3-methylphenyl)-1,5-dihydro-2H-pyrrol-2-one | RACEMATE | 204 |
| 17 | 4-acetyl-1-(4-bromophenyl)-5-cyclohexyl-3-hydroxy-1,5-dihydro-2H-pyrrol-2-one | RACEMATE | 229 |
| 18 | (R)-4-acetyl-5-cyclohexyl-3-hydroxy-1-(4-methylphenyl)-1,5-dihydro-2H-pyrrol-2-one | CHIRAL (Racemate = no. 10) | (314) |
| 19 | 4-acetyl-5-(1,2-dimethylbutyl)-3-hydroxy-1-(4-methylphenyl)-1,5-dihydro-2H-pyrrol-2-one | MIXTURE | 176 |
| 20 | 4-acetyl-5-(4-bromophenyl)-3-hydroxy-1-(4-methylphenyl)-1,5-dihydro-2H-pyrrol-2-one | RACEMATE | 206 |
| 21 | 4-acetyl-5-cyclopropyl-3-hydroxy-1-(4-methylphenyl)-1,5-dihydro-2H-pyrrol-2-one | RACEMATE | 198 |
| 22 | 5-cyclohexyl-3-hydroxy-1-(4-methylphenyl)-4-(thien-2-ylcarbonyl)-1,5-dihydro-2H-pyrrol-2-one | RACEMATE | 218 |
| 23 | 4-acetyl-5-cyclohexyl-3-hydroxy-1-phenyl-1,5-dihydro-2H-pyrrol-2-one | RACEMATE | 220 |
| 24 | 4-acetyl-1-(4-chlorophenyl)-5-cyclohexyl-3-hydroxy-1,5-dihydro-2H-pyrrol-2-one | RACEMATE | 229 |
| 25 | 4-acetyl-5-cyclohexyl-1-(4-fluorophenyl)-3-hydroxy-1,5-dihydro-2H-pyrrol-2-one | RACEMATE | 214 |
| 26 | 4-acetyl-5-(4-fluorophenyl)-3-hydroxy-1-(4-methylbenzyl)-1,5-dihydro-2H-pyrrol-2-one | RACEMATE | (340.2) |
| 27 | 4-acetyl-5-(4-bromophenyl)-3-hydroxy-1-(4-methylbenzyl)-1,5-dihydro-2H-pyrrol-2-one | RACEMATE | (400.2) |
| 28 | 4-acetyl-1-benzyl-3-hydroxy-5-(4-methylphenyl)-1,5-dihydro-2H-pyrrol-2-one | RACEMATE | (322.2) |
| 29 | 4-acetyl-5-(4-fluorophenyl)-3-hydroxy-1-(1-naphthylmethyl)-1,5-dihydro-2H-pyrrol-2-one | RACEMATE | (376.2) |
| 30 | 4-acetyl-5-(4-bromophenyl)-3-hydroxy-1-(1-naphthylmethyl)-1,5-dihydro-2H-pyrrol-2-one | RACEMATE | (436.2) |
| 31 | 4-acetyl-5-(4-fluorophenyl)-3-hydroxy-1-[4-(trifluoromethyl)benzyl]-1,5-dihydro-2H-pyrrol-2-one | RACEMATE | (394.2) |
| 32 | 4-acetyl-5-(4-bromophenyl)-1-(3,5-difluorobenzyl)-3-hydroxy-1,5-dihydro-2H-pyrrol-2-one | RACEMATE | (422.2) |
| 33 | 4-acetyl-1-benzyl-3-hydroxy-5-propyl-1,5-dihydro-2H-pyrrol-2-one | RACEMATE | (274.2) |
| 34 | 4-acetyl-1-benzyl-3-hydroxy-5-isobutyl-1,5-dihydro-2H-pyrrol-2-one | RACEMATE | (288.2) |
| 35 | 4-acetyl-5-cyclohexyl-3-hydroxy-1-[4-(trifluoromethyl)benzyl]-1,5-dihydro-2H-pyrrol-2-one | RACEMATE | (382.2) |
| 36 | 4-acetyl-5-(2-furyl)-3-hydroxy-1-[4-(trifluoromethyl)benzyl]-1,5-dihydro-2H-pyrrol-2-one | RACEMATE | (366.2) |

TABLE 1-continued

| Cpd. No. | Name | stereochemistry | melting point in °C. or (mass spec) |
|---|---|---|---|
| 37 | 4-acetyl-5-cyclohexyl-1-(3,5-difluorobenzyl)-3-hydroxy-1,5-dihydro-2H-pyrrol-2-one | RACEMATE | (350.2) |
| 38 | 4-acetyl-1-(3,5-difluorobenzyl)-5-(2-furyl)-3-hydroxy-1,5-dihydro-2H-pyrrol-2-one | RACEMATE | (334.2) |
| 39 | 4-acetyl-3-hydroxy-1-(4-methylphenyl)-5-(1-propylbutyl)-1,5-dihydro-2H-pyrrol-2-one | RACEMATE | 189 |
| 40 | 4-acetyl-3-hydroxy-5-isobutyl-1-(4-methylphenyl)-1,5-dihydro-2H-pyrrol-2-one | RACEMATE | 153 |
| 41 | 5-cyclohexyl-4-(2,2-dimethylpropanoyl)-3-hydroxy-1-(4-methylphenyl)-1,5-dihydro-2H-pyrrol-2-one | RACEMATE | 188 |
| 42 | 1-benzyl-5-(4-bromophenyl)-4-(2,2-dimethylpropanoyl)-3-hydroxy-1,5-dihydro-2H-pyrrol-2-one | RACEMATE | 198 |
| 43 | 4-acetyl-1-(3-chlorophenyl)-5-cyclohexyl-3-hydroxy-1,5-dihydro-2H-pyrrol-2-one | RACEMATE | 230 |
| 44 | 4-acetyl-1-(3-bromophenyl)-5-cyclohexyl-3-hydroxy-1,5-dihydro-2H-pyrrol-2-one | RACEMATE | 239 |
| 45 | 4-acetyl-5-cyclohexyl-1-(2-fluorophenyl)-3-hydroxy-1,5-dihydro-2H-pyrrol-2-one | RACEMATE | 238 |
| 46 | 4-butyryl-1-(4-chlorophenyl)-5-cyclohexyl-3-hydroxy-1,5-dihydro-2H-pyrrol-2-one | RACEMATE | 197 |
| 47 | 4-acetyl-5-cyclohexyl-1-(3-fluoro-4-methylphenyl)-3-hydroxy-1,5-dihydro-2H-pyrrol-2-one | RACEMATE | 203 |
| 48 | 4-acetyl-5-cyclohexyl-1-(3,4-dichlorophenyl)-3-hydroxy-1,5-dihydro-2H-pyrrol-2-one | RACEMATE | 228 |
| 49 | 4-acetyl-5-cyclohexyl-3-hydroxy-1-[4-(trifluoromethyl)phenyl]-1,5-dihydro-2H-pyrrol-2-one | RACEMATE | 235 |
| 50 | 4-acetyl-5-(cyclohex-2-en-1-yl)-3-hydroxy-1-(4-methylphenyl)-1,5-dihydro-2H-pyrrol-2-one | MIXTURE | 226 |
| 51 | (R)-4-acetyl-1-(4-chlorophenyl)-5-cyclohexyl-3-hydroxy-1,5-dihydro-2H-pyrrol-2-one | CHIRAL (Racemate = no. 24) | (334) |
| 52 | 4-acetyl-5-cyclohexyl-3-hydroxy-1-(4-isopropylphenyl)-1,5-dihydro-2H-pyrrol-2-one | RACEMATE | 227 |
| 53 | 4-acetyl-1-(4-chloro-3-methylphenyl)-5-cyclohexyl-3-hydroxy-1,5-dihydro-2H-pyrrol-2-one | RACEMATE | 217 |
| 54 | 4-acetyl-5-cyclohexyl-1-(2-fluoro-4-methylphenyl)-3-hydroxy-1,5-dihydro-2H-pyrrol-2-one | RACEMATE | 205 |
| 55 | 4-acetyl-1-[4-chloro-3-(trifluoromethyl)phenyl]-5-cyclohexyl-3-hydroxy-1,5-dihydro-2H-pyrrol-2-one | RACEMATE | 230 |
| 56 | 4-acetyl-5-cyclopentyl-3-hydroxy-1-(4-methylphenyl)-1,5-dihydro-2H-pyrrol-2-one | RACEMATE | 186 |
| 57 | 4-acetyl-5-cyclooctyl-3-hydroxy-1-(4-methylphenyl)-1,5-dihydro-2H-pyrrol-2-one | RACEMATE | 287 |
| 58 | 4-acetyl-5-(1-adamantyl)-3-hydroxy-1-(4-methylphenyl)-1,5-dihydro-2H-pyrrol-2-one | RACEMATE | 251 |
| 59 | 4-acetyl-1-(3-chloro-4-methylphenyl)-5-cyclohexyl-3-hydroxy-1,5-dihydro-2H-pyrrol-2-one | RACEMATE | (348.1) |
| 60 | 4-acetyl-5-cyclohexyl-3-hydroxy-1-(3,4,5-trichlorophenyl)-1,5-dihydro-2H-pyrrol-2-one | RACEMATE | (402) |
| 61 | 4-acetyl-3-amino-5-cyclohexyl-1-(4-methylphenyl)-1,5-dihydro-2H-pyrrol-2-one | RACEMATE | (313) |
| 62 | 4-acetyl-5-cyclohexyl-1-(2,4-difluorophenyl)-3-hydroxy-1,5-dihydro-2H-pyrrol-2-one | RACEMATE | (336.1) |
| 63 | 4-acetyl-5-cyclohexyl-1-(2,3-dihydro-1H-inden-5-yl)-3-hydroxy-1,5-dihydro-2H-pyrrol-2-one | RACEMATE | 210 |
| 64 | 4-acetyl-5-cyclohexyl-1-(4-fluoro-3-methylphenyl)-3-hydroxy-1,5-dihydro-2H-pyrrol-2-one | RACEMATE | 220 |
| 65 | 4-acetyl-5-cyclohexyl-1-(3,4-dimethylphenyl)-3-hydroxy-1,5-dihydro-2H-pyrrol-2-one | RACEMATE | 205 |
| 66 | 4-acetyl-1-(4-chloro-3-nitrophenyl)-5-cyclohexyl-3-hydroxy-1,5-dihydro-2H-pyrrol-2-one | RACEMATE | (379.1) |
| 67 | 1-(4-chlorophenyl)-5-cyclohexyl-3-hydroxy-4-[3-(4-hydroxyphenyl)propanoyl]-1,5-dihydro-2H-pyrrol-2-one | RACEMATE | 259 |
| 68 | 4-acetyl-5-cycloheptyl-3-hydroxy-1-(4-methylphenyl)-1,5-dihydro-2H-pyrrol-2-one | RACEMATE | 214 |
| 69 | 4-acetyl-1-(4-chloro-3-methylphenyl)-5-cyclopentyl-3-hydroxy-1,5-dihydro-2H-pyrrol-2-one | RACEMATE | 199 |
| 70 | 4-acetyl-1-(4-chloro-3-ethylphenyl)-5-cyclohexyl-3-hydroxy-1,5-dihydro-2H-pyrrol-2-one | RACEMATE | 225 |
| 71 | 4-acetyl-1-(3-amino-4-chlorophenyl)-5-cyclohexyl-3-hydroxy-1,5-dihydro-2H-pyrrol-2-one | RACEMATE | 162 |
| 72 | 4-acetyl-1-(4-chloro-2-fluorophenyl)-5-cyclohexyl-3-hydroxy-1,5-dihydro-2H-pyrrol-2-one | RACEMATE | (352.1) |

TABLE 1-continued

| Cpd. No. | Name | stereochemistry | melting point in ° C. or (mass spec) |
|---|---|---|---|
| 73 | 4-acetyl-1-(3-bromo-4-methylphenyl)-5-cyclohexyl-3-hydroxy-1,5-dihydro-2H-pyrrol-2-one | RACEMATE | (392) |
| 74 | 4-acetyl-1-(3,4-dimethylphenyl)-3-hydroxy-5-propyl-1,5-dihydro-2H-pyrrol-2-one | RACEMATE | (288) |
| 75 | 4-acetyl-1-(3,4-dimethylphenyl)-3-hydroxy-5-pentyl-1,5-dihydro-2H-pyrrol-2-one | RACEMATE | (316) |
| 76 | 4-acetyl-1-(3-chloro-4-methylphenyl)-3-hydroxy-5-propyl-1,5-dihydro-2H-pyrrol-2-one | RACEMATE | (308) |
| 77 | 4-acetyl-5-cyclohexyl-1-(4-ethylphenyl)-3-hydroxy-1,5-dihydro-2H-pyrrol-2-one | RACEMATE | (328) |
| 78 | 4-acetyl-3-hydroxy-1-(4-methylphenyl)-5-neopentyl-1,5-dihydro-2H-pyrrol-2-one | RACEMATE | (302) |
| 79 | 4-acetyl-5-bicyclo[2.2.1]hept-5-en-2-yl-3-hydroxy-1-(4-methylphenyl)-1,5-dihydro-2H-pyrrol-2-one | MIXTURE | (324) |
| 80 | 4-acetyl-1-(3-bromo-4-methylphenyl)-3-hydroxy-5-thien-3-yl-1,5-dihydro-2H-pyrrol-2-one | RACEMATE | (392) |
| 81 | 4-acetyl-1-benzyl-5-(cyclohexylmethyl)-3-hydroxy-1,5-dihydro-2H-pyrrol-2-one | RACEMATE | 196 |
| 82 | 4-acetyl-3-hydroxy-1-(4-methylbenzyl)-5-phenyl-1,5-dihydro-2H-pyrrol-2-one | RACEMATE | (322) |
| 83 | 4-acetyl-3-hydroxy-1-(4-methylbenzyl)-5-(4-methylphenyl)-1,5-dihydro-2H-pyrrol-2-one | RACEMATE | (336) |
| 84 | 4-[3-acetyl-4-hydroxy-1-(4-methylbenzyl)-5-oxo-2,5-dihydro-1H-pyrrol-2-yl]benzonitrile | RACEMATE | (347) |
| 85 | 4-acetyl-3-hydroxy-1-(1-naphthylmethyl)-5-phenyl-1,5-dihydro-2H-pyrrol-2-one | RACEMATE | (358) |
| 86 | 4-acetyl-3-hydroxy-5-(4-methylphenyl)-1-(1-naphthylmethyl)-1,5-dihydro-2H-pyrrol-2-one | RACEMATE | (372) |
| 87 | 4-acetyl-1-(3,5-dichlorobenzyl)-5-(4-fluorophenyl)-3-hydroxy-1,5-dihydro-2H-pyrrol-2-one | RACEMATE | (394) |
| 88 | 4-acetyl-3-hydroxy-5-phenyl-1-[4-(trifluoromethyl)benzyl]-1,5-dihydro-2H-pyrrol-2-one | RACEMATE | (376) |
| 89 | 4-acetyl-5-(4-bromophenyl)-3-hydroxy-1-[4-(trifluoromethyl)benzyl]-1,5-dihydro-2H-pyrrol-2-one | RACEMATE | (454) |
| 90 | 4-acetyl-5-(4-fluorophenyl)-3-hydroxy-1-(3-methoxybenzyl)-1,5-dihydro-2H-pyrrol-2-one | RACEMATE | (356) |
| 91 | 4-acetyl-5-(4-bromophenyl)-3-hydroxy-1-(3-methoxybenzyl)-1,5-dihydro-2H-pyrrol-2-one | RACEMATE | (416) |
| 92 | 4-acetyl-1-(3,5-difluorobenzyl)-3-hydroxy-5-phenyl-1,5-dihydro-2H-pyrrol-2-one | RACEMATE | (344) |
| 93 | 4-acetyl-1-(3,5-difluorobenzyl)-5-(4-fluorophenyl)-3-hydroxy-1,5-dihydro-2H-pyrrol-2-one | RACEMATE | (362) |
| 94 | 4-acetyl-1-(3,5-difluorobenzyl)-3-hydroxy-5-(4-methylphenyl)-1,5-dihydro-2H-pyrrol-2-one | RACEMATE | (358) |
| 95 | 4-acetyl-1-benzyl-3-hydroxy-5-neopentyl-1,5-dihydro-2H-pyrrol-2-one | RACEMATE | (302) |
| 96 | 4-acetyl-1-benzyl-3-hydroxy-5-(3,3,3-trifluoropropyl)-1,5-dihydro-2H-pyrrol-2-one | RACEMATE | (328) |
| 97 | 4-acetyl-5-cyclohexyl-1-(3-fluorophenyl)-3-hydroxy-1,5-dihydro-2H-pyrrol-2-one | RACEMATE | 210 |
| 98 | 4-butyryl-5-cyclohexyl-3-hydroxy-1-(4-methylphenyl)-1,5-dihydro-2H-pyrrol-2-one | RACEMATE | 237 |
| 99 | 4-acetyl-1-cyclohexyl-3-hydroxy-5-(4-methylphenyl)-1,5-dihydro-2H-pyrrol-2-one | RACEMATE | 210 |
| 100 | 5-cyclohexyl-4-hexanoyl-3-hydroxy-1-(4-methylphenyl)-1,5-dihydro-2H-pyrrol-2-one | RACEMATE | 213 |
| 101 | 1-(4-chlorophenyl)-5-cyclohexyl-3-hydroxy-4-(3-phenylpropanoyl)-1,5-dihydro-2H-pyrrol-2-one | RACEMATE | 227 |
| 102 | 1-(4-bromophenyl)-5-cyclohexyl-3-hydroxy-4-(3-phenylpropanoyl)-1,5-dihydro-2H-pyrrol-2-one | RACEMATE | 244 |
| 103 | 1-(4-chlorophenyl)-5-cyclohexyl-4-hexanoyl-3-hydroxy-1,5-dihydro-2H-pyrrol-2-one | RACEMATE | 211 |
| 104 | 1-(4-chlorophenyl)-5-cyclohexyl-3-hydroxy-4-pentanoyl-1,5-dihydro-2H-pyrrol-2-one | RACEMATE | 121 |
| 105 | 4-acetyl-5-cyclohexyl-1-(4-fluoro-3-nitrophenyl)-3-hydroxy-1,5-dihydro-2H-pyrrol-2-one | RACEMATE | 254 |
| 106 | 4-acetyl-3-hydroxy-1-(4-methylphenyl)-5-(thien-3-yl)-1,5-dihydro-2H-pyrrol-2-one | RACEMATE | 241 |
| 107 | 4-acetyl-(3-bromo-4-methylphenyl)-3-hydroxy-5-propyl-1,5-dihydro-2H-pyrrol-2-one | RACEMATE | (352) |
| 108 | 4-acetyl-1-(3,4-dimethylphenyl)-3-hydroxy-5-isobutyl-1,5-dihydro-2H-pyrrol-2-one | RACEMATE | (302) |
| 109 | 4-acetyl-1-(3-fluoro-4-methylphenyl)-3-hydroxy-5-propyl-1,5-dihydro-2H-pyrrol-2-one | RACEMATE | (292) |

TABLE 1-continued

| Cpd. No. | Name | stereochemistry | melting point in ° C. or (mass spec) |
|---|---|---|---|
| 110 | 4-acetyl-1-(3-fluoro-4-methylphenyl)-3-hydroxy-5-pentyl-1,5-dihydro-2H-pyrrol-2-one | RACEMATE | (320) |
| 111 | 4-acetyl-1-(3-chloro-4-methylphenyl)-3-hydroxy-5-pentyl-1,5-dihydro-2H-pyrrol-2-one | RACEMATE | (336) |
| 112 | 4-acetyl-1-(3-chloro-4-methylphenyl)-3-hydroxy-5-isobutyl-1,5-dihydro-2H-pyrrol-2-one | RACEMATE | (322) |
| 113 | 4-acetyl-1-(2,3-dihydro-1H-inden-5-yl)-3-hydroxy-5-pentyl-1,5-dihydro-2H-pyrrol-2-one | RACEMATE | (328) |
| 114 | 4-acetyl-3-hydroxy-1-(3-methylphenyl)-5-neopentyl-1,5-dihydro-2H-pyrrol-2-one | RACEMATE | (302) |
| 115 | 4-acetyl-1-(3-bromo-4-methylphenyl)-3-hydroxy-5-(3,3,3-trifluoropropyl)-1,5-dihydro-2H-pyrrol-2-one | RACEMATE | (406) |
| 116 | 4-acetyl-1-(3,4-dimethylphenyl)-3-hydroxy-5-neopentyl-1,5-dihydro-2H-pyrrol-2-one | RACEMATE | (316) |
| 117 | 4-acetyl-1-(3,4-dimethylphenyl)-3-hydroxy-5-(thien-3-yl)-1,5-dihydro-2H-pyrrol-2-one | RACEMATE | (328) |
| 118 | 4-acetyl-1-(4-chlorophenyl)-5-cyclopentyl-3-hydroxy-1,5-dihydro-2H-pyrrol-2-one | RACEMATE | 182 |
| 119 | 4-acetyl-1-(4-chloro-2-fluorophenyl)-5-cyclopentyl-3-hydroxy-1,5-dihydro-2H-pyrrol-2-one | RACEMATE | 194 |
| 120 | 4-acetyl-1-(4-chloro-2,6-difluorophenyl)-5-cyclohexyl-3-hydroxy-1,5-dihydro-2H-pyrrol-2-one | RACEMATE | (370) |
| 121 | 4-acetyl-5-bicyclo[2.2.1]hept-5-en-2-yl-1-(4-chlorophenyl)-3-hydroxy-1,5-dihydro-2H-pyrrol-2-one | MIXTURE | 196 |
| 122 | 4-benzoyl-1-benzyl-3,5-dihydroxy-5-phenyl-1,5-dihydro-2H-pyrrol-2-one | RACEMATE | 114 |
| 123 | 4-acetyl-1-benzyl-5-ethyl-3-hydroxy-1,5-dihydro-2H-pyrrol-2-one | RACEMATE | 182 |
| 124 | 4-acetyl-1-benzyl-5-(2,4-dichlorophenyl)-3-hydroxy-1,5-dihydro-2H-pyrrol-2-one | RACEMATE | 198 |
| 125 | (R)-4-acetyl-1-(4-chloro-2-fluorophenyl)-5-cyclohexyl-3-hydroxy-1,5-dihydro-2H-pyrrol-2-one | CHIRAL (Racemate = no. 72) | (352) |
| 126 | 2-cyclohexyl-4-hydroxy-N-methyl-1-(4-methylphenyl)-5-oxo-2,5-dihydro-1H-pyrrole-3-carboxamide | RACEMATE | (329) |
| 127 | 4-acetyl-1-(4-chlorophenyl)-3-hydroxy-5-(4-methylenecyclohexyl)-1,5-dihydro-2H-pyrrol-2-one | RACEMATE | 195 |
| 128 | 1-(4-chlorophenyl)-5-cyclohexyl-3-hydroxy-4-(methylthio)-1,5-dihydro-2H-pyrrol-2-one | RACEMATE | 120 |
| 129 | (R)-4-acetyl-1-(4-chloro-2-fluorophenyl)-5-cyclopentyl-3-hydroxy-1,5-dihydro-2H-pyrrol-2-one | CHIRAL (Racemate = no. 119) | 186 |
| 130 | (S)-4-acetyl-1-(4-chloro-2-fluorophenyl)-5-cyclopentyl-3-hydroxy-1,5-dihydro-2H-pyrrol-2-one | CHIRAL (Racemate = no. 119) | 188 |
| 131 | 2-cyclohexyl-4-hydroxy-1-(4-methylphenyl)-5-oxo-2,5-dihydro-1H-pyrrole-3-carboxamide | RACEMATE | (314) |
| 132 | 4-acetyl-1-(4-chlorophenyl)-3-hydroxy-5-(4-methoxycyclohexyl)-1,5-dihydro-2H-pyrrol-2-one | RACEMATE | 233 |
| 133 | 5-cyclohexyl-3-hydroxy-1-(4-methylphenyl)-4-pent-4-enoyl-1,5-dihydro-2H-pyrrol-2-one | RACEMATE | (353) |
| 134 | 4-acetyl-1-(4-chlorophenyl)-5-(cyclopentylmethyl)-3-hydroxy-1,5-dihydro-2H-pyrrol-2-one | RACEMATE | 209 |
| 135 | (R)-4-acetyl-1-(4-chloro-3-methylphenyl)-5-cyclopentyl-3-hydroxy-1,5-dihydro-2H-pyrrol-2-one | CHIRAL (Racemate = no. 69) | 135 |
| 136 | 4-acetyl-1-(4-chlorophenyl)-3-hydroxy-5-(4-methoxycyclohexyl)-1,5-dihydro-2H-pyrrol-2-one | RACEMATE | (364) |
| 137 | (R)-4-acetyl-5-cyclopentyl-1-(4-fluorophenyl)-3-hydroxy-1,5-dihydro-2H-pyrrol-2-one | CHIRAL | 118 |
| 138 | 4-acetyl-1-(4-chlorophenyl)-5-(1,4-dioxaspiro[4.5]dec-8-yl)-3-hydroxy-1,5-dihydro-2H-pyrrol-2-one | RACEMATE | 196 |
| 139 | (R)-4-acetyl-5-cyclohexyl-1-(4-fluorophenyl)-3-hydroxy-1,5-dihydro-2H-pyrrol-2-one | CHIRAL (Racemate = no. 25) | 160 |
| 140 | (R)-4-acetyl-1-(4-bromophenyl)-5-cyclohexyl-3-hydroxy-1,5-dihydro-2H-pyrrol-2-one | CHIRAL (Racemate = no. 17) | 98 |
| 141 | 4-acetyl-1-(4-chlorophenyl)-3-hydroxy-5-(3-noradamantyl)-1,5-dihydro-2H-pyrrol-2-one | RACEMATE | 230 |
| 142 | 4-acetyl-1-(4-bromo-2-fluorophenyl)-5-cyclohexyl-3-hydroxy-1,5-dihydro-2H-pyrrol-2-one | RACEMATE | 228 |

TABLE 1-continued

| Cpd. No. | Name | stereochemistry | melting point in °C. or (mass spec) |
|---|---|---|---|
| 143 | 5-cyclohexyl-3-hydroxy-1-(4-methylphenyl)-4-[5-(5-methyl-2-phenyl-1,3-oxazol-4-yl)pentanoyl]-1,5-dihydro-2H-pyrrol-2-one | RACEMATE | (513) |
| 144 | (R)-4-acetyl-1-(4-chlorophenyl)-5-cyclopentyl-3-hydroxy-1,5-dihydro-2H-pyrrol-2-one | CHIRAL (Racemate = no. 118) | (318) |
| 145 | 4-acetyl-1-(4-chlorophenyl)-3-hydroxy-5-(3,3,5,5-tetramethylcyclohexyl)-1,5-dihydro-2H-pyrrol-2-one | RACEMATE | (390) |
| 146 | 5-cyclohexyl-3-hydroxy-1-(4-methylphenyl)-4-[(4E)-5-(5-methyl-2-phenyl-1,3-oxazol-4-yl)pent-4-enoyl]-1,5-dihydro-2H-pyrrol-2-one | RACEMATE | 185 |
| 147 | (S)-4-acetyl-1-(4-chloro-2,6-difluorophenyl)-5-cyclohexyl-3-hydroxy-1,5-dihydro-2H-pyrrol-2-one | CHIRAL (Racemate = no. 120) | (368) |
| 148 | (R)-4-acetyl-1-(4-chloro-2,6-difluorophenyl)-5-cyclohexyl-3-hydroxy-1,5-dihydro-2H-pyrrol-2-one | CHIRAL (Racemate = no. 120) | 90 |
| 149 | (R)-4-acetyl-1-(4-bromo-2-fluorophenyl)-5-cyclohexyl-3-hydroxy-1,5-dihydro-2H-pyrrol-2-one | CHIRAL (Racemate = no. 142) | 96 |
| 150 | 4-acetyl-1-(4-chlorophenyl)-3-hydroxy-5-(4-methylcyclohexyl)-1,5-dihydro-2H-pyrrol-2-one | RACEMATE | 186 |
| 151 | 4-acetyl-1-(4-chloro-2-fluorophenyl)-3-hydroxy-5-(3-noradamantyl)-1,5-dihydro-2H-pyrrol-2-one | RACEMATE | 246 |
| 152 | 4-acetyl-5-(4-tert-butylcyclohexyl)-1-(4-chlorophenyl)-3-hydroxy-1,5-dihydro-2H-pyrrol-2-one | RACEMATE | 188 |
| 153 | 4-acetyl-1-(4-chloro-2-fluorophenyl)-3-hydroxy-5-(4-methylenecyclohexyl)-1,5-dihydro-2H-pyrrol-2-one | RACEMATE | 182 |
| 154 | 4-acetyl-1-(4-bromo-2,6-difluorophenyl)-5-cyclohexyl-3-hydroxy-1,5-dihydro-2H-pyrrol-2-one | RACEMATE | 170 |
| 155 | (R)-4-acetyl-1-(4-bromo-2,6-difluorophenyl)-5-cyclohexyl-3-hydroxy-1,5-dihydro-2H-pyrrol-2-one | CHIRAL (Racemate = no. 154) | 91 |
| 156 | (R)-4-acetyl-1-(4-chlorophenyl)-3-hydroxy-5-tricyclo[3.3.1.0~3,7~]non-3-yl-1,5-dihydro-2H-pyrrol-2-one | CHIRAL (Racemate = no. 141) | 178 |
| 157 | 4-acetyl-1-(4-chlorophenyl)-5-cyclohexyl-3-mercapto-1,5-dihydro-2H-pyrrol-2-one | RACEMATE | 126 |
| 158 | 1-(4-chlorophenyl)-4-(cyclohexylcarbonyl)-3-hydroxy-1,5-dihydro-2H-pyrrol-2-one | RACEMATE | (318) |
| 159 | 4-acetyl-5-(4-fluorophenyl)-3-hydroxy-1-(4-methylphenyl)-1,5-dihydro-2H-pyrrol-2-one | RACEMATE | 232 |
| 160 | 4-acetyl-3-hydroxy-1-(4-methylphenyl)-5-phenyl-1,5-dihydro-2H-pyrrol-2-one | RACEMATE | 220 |
| 161 | (S)-4-acetyl-5-cyclohexyl-3-hydroxy-1-(4-methylphenyl)-1,5-dihydro-2H-pyrrol-2-one | CHIRAL (Racemate = no. 10) | (314) |
| 162 | methyl 2-cyclohexyl-4-hydroxy-1-(4-methylphenyl)-5-oxo-2,5-dihydro-1H-pyrrole-3-carboxylate | RACEMATE | 254 |
| 163 | (S)-4-acetyl-1-(4-chlorophenyl)-5-cyclohexyl-3-hydroxy-1,5-dihydro-2H-pyrrol-2-one | CHIRAL (Racemate = no. 24) | (334) |
| 164 | 1-(4-bromophenyl)-5-cyclohexyl-4-hexanoyl-3-hydroxy-1,5-dihydro-2H-pyrrol-2-one | RACEMATE | 218 |
| 165 | ethyl 2-cyclohexyl-4-hydroxy-1-(4-methylphenyl)-5-oxo-2,5-dihydro-1H-pyrrole-3-carboxylate | RACEMATE | (344) |
| 166 | N-(3-chlorophenyl)-2-cyclohexyl-4-hydroxy-1-(4-methylphenyl)-5-oxo-2,5-dihydro-1H-pyrrole-3-carboxamide | RACEMATE | (425) |
| 167 | N-butyl-2-cyclohexyl-4-hydroxy-1-(4-methylphenyl)-5-oxo-2,5-dihydro-1H-pyrrole-3-carboxamide | RACEMATE | (369) |
| 168 | 2-cyclohexyl-4-hydroxy-1-(4-methylphenyl)-5-oxo-2,5-dihydro-1H-pyrrole-3-carboxamide | RACEMATE | (314) |
| 169 | 4-acetyl-1-(4-chloro-2-fluorophenyl)-5-cyclohexyl-3-sulfanyl-1,5-dihydro-2H-pyrrol-2-one | RACEMATE | 66 |
| 170 | 4-acetyl-1-(5-chloro-2-thienyl)-5-cyclohexyl-3-hydroxy-1,5-dihydro-2H-pyrrol-2-one | RACEMATE | 226 |
| 171 | 4-acetyl-1-(6-chloro-3-pyridinyl)-5-cyclohexyl-3-hydroxy-1,5-dihydro-2H-pyrrol-2-one | RACEMATE | 224 |
| 172 | 4-acetyl-1-(5-chloro-2-pyridinyl)-5-cyclohexyl-3-hydroxy-1,5-dihydro-2H-pyrrol-2-one | RACEMATE | 214 |

EXAMPLE 4

Binding Assay

Antagonism of the CCR2 receptor is determined by a binding assay using the human monocytic cell line THP-1. Cells are suspended in assay buffer (RPMI+1% BSA+25 mM HEPES) at $3\times10^6$ cells/ml and an aliquot (180 µl) added to a 0.5 ml siliconized Eppendorf tube. Compound (10 µl) is added at various concentrations to the cell suspension and 10 µl of $^{125}$I-MCP-1 added to give a final concentration of 0.1 nM. After incubation for 1 hr at room temperature, the cell suspension is centrifuged through oil and the cell pellets counted to quantitate cell-bound ligand. Nonspecific (NS) binding of radioligand is determined by the addition of 100 nM cold MCP-1. Control binding is determined by the addition of buffer without compound. Inhibition of $^{125}$I-MCP-1 binding to THP-1 cells was determined as an IC50 Compounds nos. 7, 8, 9, 10, 13, 14, 16, 17, 18, 19, 20, 23, 24, 25, 39, 40, 41, 43, 44, 47, 48, 49, 50, 51, 52, 53, 54, 55, 56, 58, 59, 61, 62, 63, 64, 65, 66, 68, 69, 70, 71, 72, 73, 74, 76, 77, 78, 79, 116, 118, 119, 120, 121, 125, 126, 127, 128, 129, 131, 132, 134, 135, 136, 137, 139, 140, 141, 142, 144, 145, 147, 148, 149, 150, 151, 153, 154, 155, 156, 157, 168, 169, 170 and 172 exhibited an IC50 of 5 µM or less.

EXAMPLE 5

Chemotaxis Assay

Antagonism of CCR2 function is determined by a chemotaxis assay. MCP-1 is prepared in buffer (Hanks+0.1% human serum albumin) at 3 nM concentration and aliquoted into the bottom chambers of a 96-well chemotaxis plate (Neuroprobe). THP-1 cells are suspended in the same buffer at $1\times10^7$ cells/ml and compound added at various concentrations to the aliquots of cells. The cell and compound mixture is added to the top of the polycarbonate membrane (5 µm pore diameter) and the chemotaxis plate incubated at 37° C. for 2 hr. After the unmigrated cells are scraped off the top of the filter, the plate is gently centrifuged and the membrane removed. Cells which migrate to the bottom chamber are quantitated by counting with a hemacytometer. Spontaneous chemotaxis is determined by measuring cell migration in the absence of chemokine. Chemotaxis of a positive control is determined by measuring cell migration without compound. Inhibition of cell chemotaxis is determined as an IC50.

Compounds nos. 10, 24, 51, 53, 69, 72, 125, and 156 exhibited an IC50 of 5 µM or less.

What is claimed is:

1. A pharmaceutical composition comprising a compound according to formula I

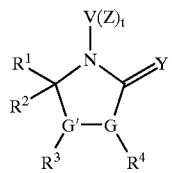

wherein,
Y is oxygen or sulfur;
G and G', together with the bond linking them, are HC—CH or C═C;
V is aryl or cycloalkyl;
Z is halogen, alkyl, alkenyl, alkynyl, hydroxyl, amino, alkoxy, aryloxy, nitro or cyano;
$R^1$ is hydrogen, halogen, alkyl, cycloalkyl, alkenyl, cycloalkenyl, alkynyl or aryl;
$R^2$ is hydrogen or hydroxy;
$R^3$ is —C(O)$R^{3a}$, —C(O)O$R^{3a}$, wherein $R^{3a}$ is hydrogen, halogen, alkyl, cycloalkyl, alkenyl, cycloalkenyl, alkynyl, aryl or heterocycle;
$R^4$ is hydroxy, sulfanyl or amino;
t is 1, 2, 3, 4 or 5;
or a pharmaceutically acceptable salt, together with a pharmaceutically acceptable diluent or carrier.

2. The composition according to claim 1 wherein in the formula I
Y is oxygen,
G and G', together with the bond linking them, are C═C,
and the meaning of V is selected from,
 a) aryl, especially phenyl, benzyl, naphthyl, naphthylmethyl, indenyl, dihydro indenyl;
 b) phenyl, benzyl, naphthyl, naphthylmethyl, indenyl or dihydro indenyl;
 c) phenyl, benzyl or dihydroindenyl;
 d) phenyl or dihydroindenyl;
 e) phenyl or benzyl; and
 f) phenyl.

3. The composition according to claim 1 wherein in the formula I
Y is oxygen,
G and G', together with the bond linking them, are C═C,
and the meaning of Z is selected from,
 a) halogen, alkyl, alkoxy, OH, $NO_2$ or $NH_2$;
 b) halogen, alkyl, alkoxy, $NO_2$ or $NH_2$;
 c) fluoro, chloro, bromo, iodo, $C_{1-4}$-alkyl, $C_{1-4}$ alkoxy, trifluoromethyl, $NO_2$ or $NH_2$;
 d) fluoro, chloro, bromo, iodo, $C_{1-4}$-alkyl, methoxy, trifluoromethyl, $NO_2$ or $NH_2$;
 e) fluoro, chloro, bromo, $C_{1-4}$-alkyl, $C_{1-4}$ alkoxy, trifluoromethyl, $NO_2$ or $NH_2$;
 f) fluoro, chloro, bromo, $C_{1-4}$-alkyl, methoxy, trifluoromethyl, $NO_2$ or $NH_2$;
 g) fluoro, chloro, bromo, iodo, $C_{1-4}$ alkyl;
 h) fluoro, chloro, bromo, iodo, methyl or ethyl;
 i) fluoro, chloro, bromo, $C_{1-4}$ alkyl; and
 j) fluoro, chloro, bromo, methyl or ethyl.

4. The composition according to claim 1 wherein in the formula I
Y is oxygen,
G and G', together with the bond linking them, are C═C,
and t is selected from,
 a) 1, 2 or 3; and
 b) 1 or 2.

5. The composition according to claim 1 wherein in the formula I
Y is oxygen,
G and G', together with the bond linking them, are C═C,
and the meaning of $R^1$ is selected from,
 a) alkyl, cycloalkyl, cycloalkenyl, or optionally substituted phenyl;
 b) $C_{1-10}$ alkyl, $C_{3-10}$ cycloalkyl, $C_{6-8}$ cycloalkenyl or optionally substituted phenyl;
 c) $C_{1-8}$ alkyl, $C_{3-10}$ cycloalkyl, $C_{6-8}$ cycloalkenyl or optionally substituted phenyl;
 d) $C_{1-8}$ alkyl, $C_{3-10}$ cycloalkyl, $C_{6-8}$ cycloalkenyl or phenyl, optionally substituted by one or more alkyl or halogen,;
 e) methyl, ethyl, propyl, i-propyl, 3,3,3-trifluoropropyl, i-butyl, t-butyl, pentyl, 1-ethylpropyl, neo-pentyl, 1,2-dimethylbutyl or 1-propylbutyl, cyclopropyl, cyclopentyl, cyclohexyl, cyclohexylmethyl, cycloheptyl, cyclooctyl, adamantyl or noradamantyl, 2-cyclohexenyl or bicyclo[2.2.1]hept-5-enyl or phenyl, optionally substituted by one or more alkyl or halogen; and f) 1-ethylpropyl, cyclohexyl, phenyl, optionally substituted by one or more methyl, fluoro, chloro, bromo or cyano.

6. The composition according to claim 1 wherein in the formula I

Y is oxygen,

G and G', together with the bond linking them, are C=C, and $R^2$ is hydrogen.

7. The composition according to claim 1 wherein in the formula I

Y is oxygen,

G and G', together with the bond linking them, are C=C, and $R^3$ is —C(O)$R^{3a}$ wherein the meaning of $R^{3a}$ is selected from,
 a) alkyl, optionally substituted aryl or heterocycle;
 b) $C_{1-5}$-alkyl, optionally substituted phenyl, benzyl, phenethyl, or thienyl; and
 c) methyl.

8. The composition according to claim 1 wherein in the formula I

Y is oxygen,

G and G', together with the bond linking them, are C=C, and $R^4$ is hydroxy.

9. The composition according to claim 1 wherein the compound of formula I is selected from acetyl-5-cyclohexyl-3-hydroxy-1-(4-methylphenyl)-1,5-dihydro-2H-pyrrol-2-one; 4-acetyl-5-(1-ethylpropyl)-3-hydroxy-1-(4-methylphenyl)-1,5-dihydro-2H-pyrrol-2-one; 4-acetyl-1-(4-bromophenyl)-5-cyclohexyl-3-hydroxy-1,5-dihydro-2H-pyrrol-2-one; (R)-4-acetyl-5-cyclohexyl-3-hydroxy-1-(4-methylphenyl)-1,5-dihydro-2H-pyrrol-2-one; 4-acetyl-1-(4-chlorophenyl)-5-cyclohexyl-3-hydroxy-1,5-dihydro-2H-pyrrol-2-one; 4-acetyl-5-cyclohexyl-1-(4-fluorophenyl)-3-hydroxy-1,5-dihydro-2H-pyrrol-2-one; (R)-4-acetyl-1-(4-chlorophenyl)-5-cyclohexyl-3-hydroxy-1,5-dihydro-2H-pyrrol-2-one; 4-acetyl-1-(4-chloro-3-methylphenyl)-5-cyclohexyl-3-hydroxy-l,5-dihydro-2H-pyrrol-2-one; 4-acetyl-5-cyclohexyl-1-(2-fluoro-4-methylphenyl)-3-hydroxy-1,5-dihydro-2H-pyrrol-2-one; 4-acetyl-5-cyclopentyl-3-hydroxy-1-(4-methylphenyl)-1,5-dihydro-2H-pyrrol-2-one; 4-acetyl-5-cyclohexyl-1-(2,3-dihydro-1H-inden-5-yl)-3-hydroxy-1,5-dihydro-2H-pyrrol-2-one; 4-acetyl-5-cyclohexyl-1-(3,4-dimethylphenyl)-3-hydroxy-1,5-dihydro-2H-pyrrol-2-one; 4-acetyl-1-(4-chloro-3-methylphenyl)-5-cyclopentyl-3-hydroxy-1,5-dihydro-2H-pyrrol-2-one; 4-acetyl-1-(4-chloro-3-ethylphenyl)-5-cyclohexyl-3-hydroxy-1,5-dihydro-2H-pyrrol-2-one; 4-acetyl-1-(4-chloro-2-fluorophenyl)-5-cyclohexyl-3-hydroxy 1,5-dihydro-2H-pyrrol-2-one; 4-acetyl-5-bicyclo[2.2.1]hept-5-en-2-yl-3-hydroxy-1-(4-methylphenyl)-l,5-dihydro-2H-pyrrol-2-one; 4-acetyl-1-(4-chlorophenyl)-5-cyclopentyl-3-hydroxy-1,5-dihydro-2H-pyrrol-2-one; 4-acetyl-1-(4-chloro-2-fluorophenyl)-5-cyclopentyl-3-hydroxy-1,5-dihydro-2H-pyrrol-2-one; 4-acetyl-1-(4-chloro-2,6-difluorophenyl)-5-cyclohexyl-3-hydroxy-1,5-dihydro-2H-pyrrol-2-one; 4-acetyl-5-bicyclo[2.2.1]hept-5-en-2-yl-1-(4-chlorophenyl)-3-hydroxy-1,5-dihydro-2H-pyrrol-2-one; (R)-4-acetyl-1-(4-chloro-2-fluorophenyl)-5-cyclohexyl-3-hydroxy-1,5-dihydro-2H-pyrrol-2-one; 4-acetyl-1-(4-chlorophenyl)-3-hydroxy-5-(4-methylenecyclohexyl)-1,5-dihydro-2H-pyrrol-2-one; (R)-4-acetyl-1-(4-chloro-2-fluorophenyl)-5-cyclopentyl-3-hydroxy-1,5-dihydro-2H-pyrrol-2-one; (R)-4-acetyl-1-(4-chloro-3-methylphenyl)-5-cyclopentyl-3-hydroxy-1,5-dihydro-2H-pyrrol-2-one; (R)-4-acetyl-5-cyclopentyl-1-(4-fluorophenyl)-3-hydroxy-1,5-dihydro-2H-pyrrol-2-one; (R)4-acetyl-5-cyclohexyl-1-(4-fluorophenyl)-3-hydroxy-1,5-dihydro-2H-pyrrol-1-2-one; (R)-4-acetyl-1-(4-bromophenyl)-5-cyclohexyl-3-hydroxy-1,5-dihydro-2H-pyrrol-2-one; 4-acetyl-1-(4-chlorophenyl)-3-hydroxy-5-(3-noradamantyl)-1,5-dihydro-2H-pyrrol-2-one;

4-acetyl-1-(4-bromo-2-fluorophenyl)-5-cyclohexyl-3-hydroxy-l,5-dihydro-2H-pyrrol-2-one; (R)-4-acetyl-1-(4-chlorophenyl)-5-cyclopentyl-3-hydroxy-1,5-dihydro-2H-pyrrol-2-one; (R)-4-acetyl-1-(4-chloro-2,6-difluorophenyl)-5-cyclohexyl-3-hydroxy-1,5-dihydro-2H-pyrrol-2-one; (R)-4-acetyl-1-(4-bromo-2-fluorophenyl)-5-cyclohexyl-3-hydroxy-1,5-dihydro-2H-pyrrol-2-one; 4-acetyl-1-(4-chlorophenyl)-3-hydroxy-5-(4-methylcyclohexyl)-1,5-dihydro-2H-pyrrol-2-one; 4-acetyl-1-(4-chloro-2-fluorophenyl)-3-hydroxy-5-(3-noradamantyl)-1,5-dihydro-2H-pyrrol-2-one; 4-acetyl-1-(4-chloro-2-fluorophenyl)-3-hydroxy-5-(4-methylenecyclohexyl)-1,5-dihydro-2H-pyrrol-2-one; 4-acetyl-1-(4-bromo-2,6-difluorophenyl)-5-cyclohexyl-3-hydroxy-1,5-dihydro-2H-pyrrol-2-one; (R)-4-acetyl-1-(4-bromo-2,6-difluorophenyl)-5-cyclohexyl-3-hydroxy-1,5-dihydro-2H-pyrrol-2-one; (R)-4-acetyl-1-(4-chlorophenyl)-3-hydroxy-5-tricyclo[3.3.1,0~3.7~]non-3-yl-1,5-dihydro-2H-pyrrol-2-one; 4-acetyl-1-(4-chlorophenyl)-5-cyclohexyl-3-mercapto-1,5-dihydro-2H-pyrrol-2-one and 4-acetyl-1-(4-chloro-2-fluorophenyl)-5-cyclohexyl-3-sulfanyl-1,5-dihydro-2H-pyrrol-2-one.

10. The composition according to claim 9 wherein the compound of formula I is selected from 4-acetyl-5-cyclohexyl-3-hydroxy-1-(4-methylphenyl)-1,5-dihydro-2H-pyrrol-2-one; 4-acetyl-1-(4-bromophenyl)-5-cyclohexyl-3-hydroxy-1,5-dihydro-2H-pyrrol-2-one; (R)-4-acetyl-5-cyclohexyl-3-hydroxy-1-(4-methylphenyl)-1,5-dihydro-2H-pyrrol-2-one; 4-acetyl-1-(4-chlorophenyl)-5-cyclohexyl-3-hydroxy-1,5-dihydro-2H-pyrrol-2-one; (R)-4-acetyl-1-(4-chlorophenyl)-5-cyclohexyl-3-hydroxy-1,5-dihydro-2H-pyrrol-2-one; 4-acetyl-1-(4-chloro-3-methylphenyl)-5-cyclohexyl-3-hydroxy-1,5-dihydro-2H-pyrrol-2-one; 4-acetyl-5-cyclohexyl-1-(2-fluoro-4-methylphenyl)-3-hydroxy-1,5-dihydro-2H-pyrrol-2-one; 4-acetyl-1-(4-chloro-3-methylphenyl)-5-cyclopentyl-3-hydroxy-1,5-dihydro-2H-pyrrol-2-one; 4-acetyl-1-(4-chloro-2-fluorophenyl)-5-cyclohexyl-3-hydroxy-1,5-dihydro-2H-pyrrol-2-one; 4-acetyl-1-(4-chlorophenyl)-5-cyclopentyl-3-hydroxy-1,5-dihydro-2H-pyrrol-2-one; 4-acetyl-1-(4-chloro-2-fluorophenyl)-5-cyclopentyl-3-hydroxy-1,5-dihydro-2H-pyrrol-2-one; 4-acetyl-1-(4-chloro-2,6-difluorohenyl)5-cyclohexyl-3-hydroxy-1,5-dihydro-2H-pyrrol-2-one; 4-acetyl-5-bicyclo[2.2.1]hept-5-en-2-yl-1-(4-chlorophenyl)-3-hydroxy-1,5-dihydro-2H-pyrrol-2-one; (R)-4-acetyl-1-(4-chloro-2-fluorophenyl)-5-cyclohexyl-3-hydroxy-1,5-dihydro-2H-pyrrol-2-one; 4-acetyl-1-(4-chlorophenyl)-3-hydroxy-S-(4-methylenecyclohexyl)-1,5-dihydro-2H-pyrrol-2-one; (R)-4-acetyl-1-(4-chloro-2-fluorophenyl)-5-cyclopentyl-3-hydroxy-1,5-dihydro-2H-pyrrol-2-one; (R)4-acetyl-1-(4-chloro-3-methylphenyl)-5-cyclopentyl-3-hydroxy-1,5-dihydro-2H-pyrrol-2-one; (R)-4-acetyl-5-(4-fluorophenyl)-3-hydroxy-1,5-dihydro-2H-pyrrol-2-one; (R)-4-acetyl-5-cyclopentyl-1-(4- fluorophenyl)-3-hydroxy-1,5-dihydro-2H-pyrrol-2-one; (R)-4-acetyl-5-cyclohexyl-1-(4-fluorophenyl)-3-hydroxy-1,5-dihydro-2H-pyrrol-2-one; (R)-4-acetyl-1-(4-bromophenyl)-5-cyclohexyl-3-hydroxyl 5-dihydro-2H-pyrrol-2-one; 4-acetyl-1-(4-chlorophenyl)-3-hydroxy-5-(3-noradamantyl)-1,5-dihydro-2H-pyrrol-2-one; 4-acetyl-1-(4-bromo-2-fluorophenyl)-5-cyclohexyl-3-hydroxy-1,5-dihydro-2H-pyrrol-2-one; (R)-4-acetyl-1-(4-chlorophenyl)-5-cyclopentyl-3-hydroxy-1,5-dihydro-2H-pyrrol-2-one; (R)-4-acetyl-1-(4-chloro-2,6-difluorophenyl)-5-cyclohexyl-3-hydroxy-1,5-dihydro-2H-pyrrol-2-one; (R)-4-acetyl-1-(4-bromo-2-fluorophenyl)-5-cyclohexyl-3-hydroxy-1,5-dihydro-2H-pyrrol-2-one; 4-acetyl-1-(4-chlorophenyl)-3-hydroxy-5-(4-methylcyclohexyl)-1,5-dihydro-2H-pyrrol-2-one; 4-acetyl-1-(4-chloro-2-fluorophenyl)-3-hydroxy-5-(3-noradamantyl)1,5-dihydro-2H-pyrrol-2-one; 4-acetyl-1-(4-chloro-2-fluorophenyl)-3-hydroxy-5-(4-methylenecyclohexyl)1,5-dihydro-2H-pyrrol-2-one; 4-acetyl-1-(4-bromo-2,6-difluorophenyl)-5-cyclohexyl-3-hydroxy-1,5-dihydro-2H-pyrrol-2-one; (R)-4-acetyl-1-(4-bromo-2,6-difluorophenyl)-5-cyclohexyl-3-hydroxy-1,5-dihydro-2H-pyrrol-2-one; (R)-4-acetyl-1-(4-chlorophenyl)-3-hydroxy-5-tricyclo[3.3.1.0~3.7~]non-3-yl-1,5-dihydro-2H-pyrrol-2-one; 4-acetyl-1-(4-chlorophenyl)-5-cyclohexyl-3-mercapto-1,5-dihydro-2H-pyrrol-2-one and 4-acetyl-1-(4-chloro-2-fluorophenyl)-5-cyclohexyl-3-sulfanyl-1,5-dihydro-2H-pyrrol-2-one.

11. The composition according to claim 10 wherein the compound of formula I is selected from (R)-4-acetyl-1-(4-chlorophenyl)-5-cyclohexyl-3-hydroxy-1,5-dihydro-2H-pyrrol-2-one; (R)-4-acetyl-1-(4-chloro-2-fluorophenyl)-5-cyclohexyl-3-hydroxy-1,5-dihydro-2H-pyrrol-2-one; (R)4-acetyl-1-(4-chloro-2-fluorophenyl)-5-cyclopentyl-3-hydroxy-1,5-dihydro-2H-pyrrol-2-one; (R)-4-acetyl-1-(4-bromophenyl)-5-cyclohexyl-3-hydroxy-1,5-dihydro-2H-pyrrol-2-one; (R)-4-acetyl-1-(4-chlorophenyl)-5-cyclopentyl-3-hydroxy-1,5-dihydro-2H-pyrrol-2-one; (R)-4-acetyl-1-(4-chloro-2,6-difluorophenyl)-5-cyclohexyl-3-hydroxy-1,5-dihydro-2H-pyrrol-2-one; (R)-4-acetyl-1-(4-bromo-2-fluorophenyl),5-cyclohexyl-3-hydroxy-1,5-dihydro-2H-pyrrol-2-one; (R)-4-acetyl-1-(4-bromo-2,6-difluorophenyl)-5-cyclohexyl-3-hydroxy-1,5-dihydro-2H-pyrrol-2-one and (R)-4-acetyl-1-(4-chlorophenyl)-3-hydroxy-5-tricyclo[3.3.1.0~3.7~]non-3-yl-1,5-dihydro-2H-pyrrol-2-one.

12. The composition according to claim 1 wherein the compound of formula I is in the form of its (−)-enantiomer.

13. The composition according to claim 1 wherein the compound of formula I is in the form of its (R)-enantiomer.

14. A compound of formula I

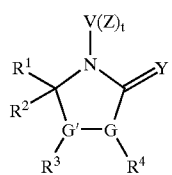

wherein,

Y is sulfur;

G and G', together with the bond linking them, are HC—CH or C=C;

V is aryl or cycloalkyl;

Z is halogen, alkyl, alkenyl, alkynyl, hydroxyl, amino, alkoxy, aryloxy, nitro or cyano;

$R^1$ is hydrogen, halogen, alkyl, cycloalkyl, alkenyl, cycloalkenyl, alkynyl or aryl;

$R^2$ is hydrogen or hydroxy;

$R^3$ is —C(C)$R^{3a}$, —C(O)O$R^{3a}$ wherein $R^{3a}$ is hydrogen, halogen, alkyl, cycloalkyl, alkenyl, cycloalkenyl, alkynyl, aryl or heterocycle;

$R^4$ is hydroxy, sulfanyl or amino; and t is 1, 2, 3, 4 or 5;

or a pharmaceutically acceptable salt.

15. A compound of formula

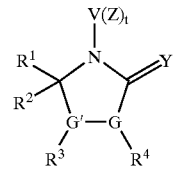

wherein,

Y is oxygen or sulfur;

G and G', together with the bond linking them, are HC—OH or C=C;

V is aryl or cycloalkyl;

Z is halogen, alkyl, alkenyl, alkynyl, hydroxyl, amino, alkoxy, aryloxy, nitro or cyano;

$R^1$ is hydrogen, halogen, alkyl, cycloalkyl, alkenyl, cycloalkenyl, alkynyl, or aryl;

$R^2$ is hydroxy;

$R^3$ is —C(O)$R^{3a}$, —C(O)O$R^{3a}$ wherein $R^{3a}$ is hydrogen, halogen, alkyl, cycloalkyl, alkenyl, cycloalkenyl, alkynyl, aryl or heterocycle;

$R^4$ is hydroxy, sulfanyl or amino;

t is 1, 2, 3, 4 or 5;

or a pharmaceutically acceptable salt.

16. A compound of formula I

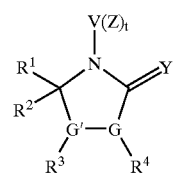

wherein

Y is oxygen or sulfur;

G and G', together with the bond linking them, are HC—CH or C=C;

V is aryl or cycloalkyl;

Z is halogen, alkyl, alkenyl, alkynyl, hydroxyl, amino, alkoxy, aryloxy, nitro or cyano;

$R^1$ is halogen, alkyl, cycloalkyl, alkenyl, cycloalkenyl, alkynyl or aryl;

$R^2$ is hydrogen;

$R^3$ is —C(O)$R^{3a}$, —C(O)O$R^{3a}$ wherein $R^{3a}$ is hydrogen, halogen, alkyl, cycloalkyl, alkenyl, cycloalkenyl, alkynyl, aryl or heterocycle;

$R^4$ is hydroxy, sulfanyl or amino;

t is 1, 2, 3, 4 or 5;

or a pharmaceutically acceptable salt, provided that $R^1$ is not $C_{1-7}$-alkyl, phenyl, $C_{3-5}$-cycloalkyl, or methylene ($C_{3-5}$-cycloalkyl), wherein each alkyl or phenyl group optionally substituted with one or two methyl, methoxy, ethyl or trifluoromethyl, or up to three halogens.

17. A compound of formula

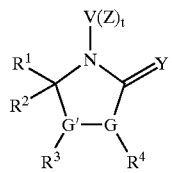

wherein,

Y is oxygen or sulfur;

G and G', together with the bond linking them, are HC—CH or C=C;

V is aryl or cycloalkyl;

Z is halogen, alkyl, alkenyl, alkynyl, hydroxyl, amino, alkoxy, aryloxy, nitro or cyano;

$R^1$ is hydrogen, halogen, alkyl, cycloalkyl, alkenyl, cycloalkenyl, alkynyl or aryl;

$R^2$ is hydrogen or hydroxy;

$R^3$ is —C(O)$R^{3a}$, —C(O)O$R^{3a}$ wherein $R^{3a}$ is hydrogen, halogen, alkyl, cycloalkyl, alkenyl, cycloalkenyl, alkynyl, aryl or heterocycle;

$R^4$ is hydroxy, sulfanyl or amino;

t is 1, 2, 3, 4 or 5;

or a pharmaceutically acceptable salt provided that one of $R^1$ and $R^2$ is other than hydrogen.

18. A compound of formula

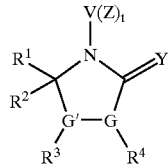

wherein,

Y is oxygen or sulfur;

G and G', together with the bond linking them, are HC—CH or C=C;

V is aryl or cycloalkyl;

Z is halogen, alkyl, alkenyl, alkynyl, hydroxyl, amino, alkoxy, aryloxy, nitro or cyano;

$R^1$ is hydrogen, halogen, alkyl, cycloalkyl, alkenyl, cycloalkenyl, alkynyl or aryl;

$R^2$ is hydrogen or hydroxy;

$R^3$ is —COR$^{3a}$, —C(O)O$R^{3a}$ wherein $R^{3a}$ is hydrogen, halogen, alkyl, cycloalkyl, alkenyl, cycloalkenyl, alkynyl, aryl or heterocycle;

$R^4$ is hydroxy, sulfanyl or amino;

t is 1, 2, 3, 4 or 5;

or a pharmaceutically acceptable salt, provided that $R^3$ is not —C(O)$R^{3a}$ wherein $R^{3a}$ is hydrogen, $C_{1-7}$-alkyl, $C_{2-3}$-alkenyl, phenyl, $C_{3-5}$-cycloalkyl, or methylene ($C_{3-5}$-cycloalkyl), wherein each alkyl, phenyl or alkenyl group optionally substituted with (a) one nitro, methoxy or ethoxy, (b) one or two methyl, ethyl or trifluoromethyl, or (c) up to three halogens.

19. A compound of formula

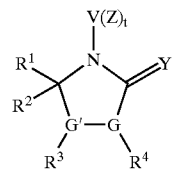

wherein

Y is oxygen or sulfur;

G and G', together with the bond linking them, are HC—CH or C=C;

V is aryl or cycloalkyl;

Z is halogen, alkyl, alkenyl, alkynyl, hydroxyl, amino, alkoxy, aryloxy, nitro or cyano;

$R^1$ is hydrogen, halogen, alkyl, cycloalkyl, alkenyl, cycloalkenyl, alkynyl or aryl;

$R^2$ is hydrogen or hydroxy;

$R^3$ is —C(O)$R^{3a}$, —C(O)O$R^{3a}$ wherein $R^{3a}$ is hydrogen, halogen, alkyl, cycloalkyl, alkenyl, cycloalkenyl, alkynyl, aryl or heterocycle;

$R^4$ is hydroxy, sulfanyl or amino;

t is 1, 2, 3, 4 or 5;

or a pharmaceutically acceptable salt, and wherein when

Y is oxygen; and

G and G', together with the bond linking them, are C=C; then $R^1$ is other than hydrogen, $C_{1-7}$-alkyl, phenyl, $C_{3-5}$-cycloalkyl, or methylene ($C_{3-5}$-cycloalkyl), wherein each alkyl or phenyl group is optionally substituted with one or two methyl, methoxy, ethyl or trifluoromethyl, or up to three halogens when $R^2$ is hydrogen; or $R^3$ is other than —C(O)$R^{3a}$ wherein $R^{3a}$ is hydrogen, $C_{1-7}$-alkyl, $C_{2-3}$-alkenyl, phenyl, $C_{3-5}$-cycloalkyl, or methylene ($C_{3-5}$-cycloalkyl), wherein each alkyl, phenyl or alkenyl group is optionally substituted with one nitro, methoxy or ethoxy, with one or two methyl, ethyl or trifluoromethyl, or with up to three halogens.

20. A compound of formula

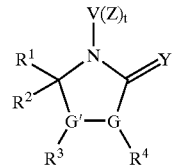

in fully or partially resolved isomeric form wherein,

Y is oxygen or sulfur;

G and G', together with the bond linking them, are HC—OH or C=C;

V is aryl or cycloalkyl;

Z is halogen, alkyl, alkenyl, alkynyl, hydroxyl, amino, alkoxy, aryloxy, nitro or cyano;

$R^1$ is hydrogen, halogen, alkyl, cycloalkyl, alkenyl, cycloalkenyl, alkynyl or aryl;

$R^2$ is hydrogen or hydroxy;

$R^3$ is —C(O)$R^{3a}$, —C(O)O$R^{3a}$ wherein $R^{3a}$ is hydrogen, halogen, alkyl, cycloalkyl, alkenyl, cycloalkenyl, alkynyl, aryl or heterocycle;

R⁴ is hydroxy, sulfanyl or amino;

t is 1, 2, 3, 4 or 5;

or a pharmaceutically acceptable salt.

21. A compound selected from one of the following compounds:

| Cpd. No. | Name |
|---|---|
| 1 | 4-acetyl-1-benzyl-5-(4-bromophenyl)-3-hydroxy-1,5-dihydro-2H-pyrrol-2-one |
| 2 | 4-acetyl-5-(4-bromophenyl)-1-(5-bromopyridin-2-yl)-3-hydroxy-1,5-dihydro-2H-pyrrol-2-one |
| 3 | 4-acetyl-1-benzyl-5-(2-fluorophenyl)-3-hydroxy-1,5-dihydro-2H-pyrrol-2-one |
| 4 | 4-acetyl-1-benzyl-5-(4-chlorophenyl)-3-hydroxy-1,5-dihydro-2H-pyrrol-2-one |
| 5 | 4-acetyl-1-benzyl-3-hydroxy-5-phenyl-1,5-dihydro-2H-pyrrol-2-one |
| 6 | 4-acetyl-1-benzyl-5-(4-fluorophenyl)-3-hydroxy-1,5-dihydro-2H-pyrrol-2-one |
| 7 | 4-acetyl-1-benzyl-5-cyclohexyl-3-hydroxy-1,5-dihydro-2H-pyrrol-2-one |
| 8 | 4-acetyl-1-benzyl-5-(2-furyl)-3-hydroxy-1,5-dihydro-2H-pyrrol-2-one |
| 9 | 4-acetyl-1,5-bis(4-bromophenyl)-3-hydroxy-1,5-dihydro-2H-pyrrol-2-one |
| 10 | 4-acetyl-5-cyclohexyl-3-hydroxy-1-(4-methylphenyl)-1,5-dihydro-2H-pyrrol-2-one |
| 11 | 4-acetyl-3-hydroxy-5-isopropyl-1-(4-methylphenyl)-1,5-dihydro-2H-pyrrol-2-one |
| 12 | 4-acetyl-5-tert-butyl-3-hydroxy-1-(4-methylphenyl)-1,5-dihydro-2H-pyrrol-2-one |
| 13 | 4-acetyl-5-(1-ethylpropyl)-3-hydroxy-1-(4-methylphenyl)-1,5-dihydro-2H-pyrrol-2-one |
| 14 | 4-acetyl-5-cyclohexyl-3-hydroxy-1-(4-methoxyphenyl)-1,5-dihydro-2H-pyrrol-2-one |
| 15 | 4-acetyl-5-(4-chlorophenyl)-3-hydroxy-1-(4-methylphenyl)-1,5-dihydro-2H-pyrrol-2-one |
| 16 | 4-acetyl-5-cyclohexyl-3-hydroxy-1-(3-methylphenyl)-1,5-dihydro-2H-pyrrol-2-one |
| 17 | 4-acetyl-1-(4-bromophenyl)-5-cyclohexyl-3-hydroxy-1,5-dihydro-2H-pyrrol-2-one |
| 18 | (R)-4-acetyl-5-cyclohexyl-3-hydroxy-1-(4-methylphenyl)-1,5-dihydro-2H-pyrrol-2-one |
| 19 | 4-acetyl-5-(1,2-dimethylbutyl)-3-hydroxy-1-(4-methylphenyl)-1,5-dihydro-2H-pyrrol-2-one |
| 20 | 4-acetyl-5-(4-bromophenyl)-3-hydroxy-1-(4-methylphenyl)-1,5-dihydro-2H-pyrrol-2-one |
| 21 | 4-acetyl-5-cyclopropyl-3-hydroxy-1-(4-methylphenyl)-1,5-dihydro-2H-pyrrol-2-one |
| 22 | 5-cyclohexyl-3-hydroxy-1-(4-methylphenyl)-4-(thien-2-ylcarbonyl)-1,5-dihydro-2H-pyrrol-2-one |
| 23 | 4-acetyl-5-cyclohexyl-3-hydroxy-1-phenyl-1,5-dihydro-2H-pyrrol-2-one |
| 24 | 4-acetyl-1-(4-chlorophenyl)-5-cyclohexyl-3-hydroxy-1,5-dihydro-2H-pyrrol-2-one |
| 25 | 4-acetyl-5-cyclohexyl-1-(4-fluorophenyl)-3-hydroxy-1,5-dihydro-2H-pyrrol-2-one |
| 26 | 4-acetyl-5-(4-fluorophenyl)-3-hydroxy-1-(4-methylbenzyl)-1,5-dihydro-2H-pyrrol-2-one |
| 27 | 4-acetyl-5-(4-bromophenyl)-3-hydroxy-1-(4-methylbenzyl)-1,5-dihydro-2H-pyrrol-2-one |
| 28 | 4-acetyl-1-benzyl-3-hydroxy-5-(4-methylphenyl)-1,5-dihydro-2H-pyrrol-2-one |
| 29 | 4-acetyl-5-(4-fluorophenyl)-3-hydroxy-1-(1-naphthylmethyl)-1,5-dihydro-2H-pyrrol-2-one |
| 30 | 4-acetyl-5-(4-bromophenyl)-3-hydroxy-1-(1-naphthylmethyl)-1,5-dihydro-2H-pyrrol-2-one |
| 31 | 4-acetyl-5-(4-fluorophenyl)-3-hydroxy-1-[4-(trifluoromethyl)benzyl]-1,5-dihydro-2H-pyrrol-2-one |
| 32 | 4-acetyl-5-(4-bromophenyl)-1-(3,5-difluorobenzyl)-3-hydroxy-1,5-dihydro-2H-pyrrol-2-one |
| 33 | 4-acetyl-1-benzyl-3-hydroxy-5-propyl-1,5-dihydro-2H-pyrrol-2-one |
| 34 | 4-acetyl-1-benzyl-3-hydroxy-5-isobutyl-1,5-dihydro-2H-pyrrol-2-one |

-continued

| Cpd. No. | Name |
|---|---|
| 35 | 4-acetyl-5-cyclohexyl-3-hydroxy-1-[4-(trifluoromethyl)benzyl]-1,5-dihydro-2H-pyrrol-2-one |
| 36 | 4-acetyl-5-(2-furyl)-3-hydroxy-1-[4-(trifluoromethyl)benzyl]-1,5-dihydro-2H-pyrrol-2-one |
| 37 | 4-acetyl-5-cyclohexyl-1-(3,5-difluorobenzyl)-3-hydroxy-1,5-dihydro-2H-pyrrol-2-one |
| 38 | 4-acetyl-1-(3,5-difluorobenzyl)-5-(2-furyl)-3-hydroxy-1,5-dihydro-2H-pyrrol-2-one |
| 39 | 4-acetyl-3-hydroxy-1-(4-methylphenyl)-5-(1-propylbutyl)-1,5-dihydro-2H-pyrrol-2-one |
| 40 | 4-acetyl-3-hydroxy-5-isobutyl-1-(4-methylphenyl)-1,5-dihydro-2H-pyrrol-2-one |
| 41 | 5-cyclohexyl-4-(2,2-dimethylpropanoyl)-3-hydroxy-1-(4-methylphenyl)-1,5-dihydro-2H-pyrrol-2-one |
| 42 | 1-benzyl-5-(4-bromophenyl)-4-(2,2-dimethylpropanoyl)-3-hydroxy-1,5-dihydro-2H-pyrrol-2-one |
| 43 | 4-acetyl-1-(3-chlorophenyl)-5-cyclohexyl-3-hydroxy-1,5-dihydro-2H-pyrrol-2-one |
| 44 | 4-acetyl-1-(3-bromophenyl)-5-cyclohexyl-3-hydroxy-1,5-dihydro-2H-pyrrol-2-one |
| 45 | 4-acetyl-5-cyclohexyl-1-(2-fluorophenyl)-3-hydroxy-1,5-dihydro-2H-pyrrol-2-one |
| 46 | 4-butyryl-1-(4-chlorophenyl)-5-cyclohexyl-3-hydroxy-1,5-dihydro-2H-pyrrol-2-one |
| 47 | 4-acetyl-5-cyclohexyl-1-(3-fluoro-4-methylphenyl)-3-hydroxy-1,5-dihydro-2H-pyrrol-2-one |
| 48 | 4-acetyl-5-cyclohexyl-1-(3,4-dichlorophenyl)-3-hydroxy-1,5-dihydro-2H-pyrrol-2-one |
| 49 | 4-acetyl-5-cyclohexyl-3-hydroxy-1-[4-(trifluoromethyl)phenyl]-1,5-dihydro-2H-pyrrol-2-one |
| 50 | 4-acetyl-5-(cyclohex-2-en-1-yl)-3-hydroxy-1-(4-methylphenyl)-1,5-dihydro-2H-pyrrol-2-one |
| 51 | (R)-4-acetyl-1-(4-chlorophenyl)-5-cyclohexyl-3-hydroxy-1,5-dihydro-2H-pyrrol-2-one |
| 52 | 4-acetyl-5-cyclohexyl-3-hydroxy-1-(4-isopropylphenyl)-1,5-dihydro-2H-pyrrol-2-one |
| 53 | 4-acetyl-1-(4-chloro-3-methylphenyl)-5-cyclohexyl-3-hydroxy-1,5-dihydro-2H-pyrrol-2-one |
| 54 | 4-acetyl-5-cyclohexyl-1-(2-fluoro-4-methylphenyl)-3-hydroxy-1,5-dihydro-2H-pyrrol-2-one |
| 55 | 4-acetyl-1-[4-chloro-3-(trifluoromethyl)phenyl]-5-cyclohexyl-3-hydroxy-1,5-dihydro-2H-pyrrol-2-one |
| 56 | 4-acetyl-5-cyclopentyl-3-hydroxy-1-(4-methylphenyl)-1,5-dihydro-2H-pyrrol-2-one |
| 57 | 4-acetyl-5-cyclooctyl-3-hydroxy-1-(4-methylphenyl)-1,5-dihydro-2H-pyrrol-2-one |
| 58 | 4-acetyl-5-(1-adamantyl)-3-hydroxy-1-(4-methylphenyl)-1,5-dihydro-2H-pyrrol-2-one |
| 59 | 4-acetyl-1-(3-chloro-4-methylphenyl)-5-cyclohexyl-3-hydroxy-1,5-dihydro-2H-pyrrol-2-one |
| 60 | 4-acetyl-5-cyclohexyl-3-hydroxy-1-(3,4,5-trichlorophenyl)-1,5-dihydro-2H-pyrrol-2-one |
| 61 | 4-acetyl-3-amino-5-cyclohexyl-1-(4-methylphenyl)-1,5-dihydro-2H-pyrrol-2-one |
| 62 | 4-acetyl-5-cyclohexyl-1-(2,4-difluorophenyl)-3-hydroxy-1,5-dihydro-2H-pyrrol-2-one |
| 63 | 4-acetyl-5-cyclohexyl-1-(2,3-dihydro-1H-inden-5-yl)-3-hydroxy-1,5-dihydro-2H-pyrrol-2-one |
| 64 | 4-acetyl-5-cyclohexyl-1-(4-fluoro-3-methylphenyl)-3-hydroxy-1,5-dihydro-2H-pyrrol-2-one |
| 65 | 4-acetyl-5-cyclohexyl-1-(3,4-dimethylphenyl)-3-hydroxy-1,5-dihydro-2H-pyrrol-2-one |
| 66 | 4-acetyl-1-(4-chloro-3-nitrophenyl)-5-cyclohexyl-3-hydroxy-1,5-dihydro-2H-pyrrol-2-one |
| 67 | 1-(4-chlorophenyl)-5-cyclohexyl-3-hydroxy-4-[3-(4-hydroxyphenyl)propanoyl]-1,5-dihydro-2H-pyrrol-2-one |
| 68 | 4-acetyl-5-cycloheptyl-3-hydroxy-1-(4-methylphenyl)-1,5-dihydro-2H-pyrrol-2-one |
| 69 | 4-acetyl-1-(4-chloro-3-methylphenyl)-5-cyclopentyl-3-hydroxy-1,5-dihydro-2H-pyrrol-2-one |
| 70 | 4-acetyl-1-(4-chloro-3-ethylphenyl)-5-cyclohexyl-3-hydroxy-1,5-dihydro-2H-pyrrol-2-one |
| 71 | 4-acetyl-1-(3-amino-4-chlorophenyl)-5-cyclohexyl-3-hydroxy-1,5-dihydro-2H-pyrrol-2-one |

| Cpd. No. | Name |
|---|---|
| 72 | 4-acetyl-1-(4-chloro-2-fluorophenyl)-5-cyclohexyl-3-hydroxy-1,5-dihydro-2H-pyrrol-2-one |
| 73 | 4-acetyl-1-(3-bromo-4-methylphenyl)-5-cyclohexyl-3-hydroxy-1,5-dihydro-2H-pyrrol-2-one |
| 74 | 4-acetyl-1-(3,4-dimethylphenyl)-3-hydroxy-5-propyl-1,5-dihydro-2H-pyrrol-2-one |
| 75 | 4-acetyl-1-(3,4-dimethylphenyl)-3-hydroxy-5-pentyl-1,5-dihydro-2H-pyrrol-2-one |
| 76 | 4-acetyl-1-(3-chloro-4-methylphenyl)-3-hydroxy-5-propyl-1,5-dihydro-2H-pyrrol-2-one |
| 77 | 4-acetyl-5-cyclohexyl-1-(4-ethylphenyl)-3-hydroxy-1,5-dihydro-2H-pyrrol-2-one |
| 78 | 4-acetyl-3-hydroxy-1-(4-methylphenyl)-5-neopentyl-1,5-dihydro-2H-pyrrol-2-one |
| 79 | 4-acetyl-5-bicyclo[2.2.1]hept-5-en-2-yl-3-hydroxy-1-(4-methylphenyl)-1,5-dihydro-2H-pyrrol-2-one |
| 80 | 4-acetyl-1-(3-bromo-4-methylphenyl)-3-hydroxy-5-thien-3-yl-1,5-dihydro-2H-pyrrol-2-one |
| 81 | 4-acetyl-1-benzyl-5-(cyclohexylmethyl)-3-hydroxy-1,5-dihydro-2H-pyrrol-2-one |
| 82 | 4-acetyl-3-hydroxy-1-(4-methylbenzyl)-5-phenyl-1,5-dihydro-2H-pyrrol-2-one |
| 83 | 4-acetyl-3-hydroxy-1-(4-methylbenzyl)-5-(4-methylphenyl)-1,5-dihydro-2H-pyrrol-2-one |
| 84 | 4-[3-acetyl-4-hydroxy-1-(4-methylbenzyl)-5-oxo-2,5-dihydro-1H-pyrrol-2-yl]benzonitrile |
| 85 | 4-acetyl-3-hydroxy-1-(1-naphthylmethyl)-5-phenyl-1,5-dihydro-2H-pyrrol-2-one |
| 86 | 4-acetyl-3-hydroxy-5-(4-methylphenyl)-1-(1-naphthylmethyl)-1,5-dihydro-2H-pyrrol-2-one |
| 87 | 4-acetyl-1-(3,5-dichlorobenzyl)-5-(4-fluorophenyl)-3-hydroxy-1,5-dihydro-2H-pyrrol-2-one |
| 88 | 4-acetyl-3-hydroxy-5-phenyl-1-[4-(trifluoromethyl)benzyl]-1,5-dihydro-2H-pyrrol-2-one |
| 89 | 4-acetyl-5-(4-bromophenyl)-3-hydroxy-1-[4-(trifluoromethyl)benzyl]-1,5-dihydro-2H-pyrrol-2-one |
| 90 | 4-acetyl-5-(4-fluorophenyl)-3-hydroxy-1-(3-methoxybenzyl)-1,5-dihydro-2H-pyrrol-2-one |
| 91 | 4-acetyl-5-(4-bromophenyl)-3-hydroxy-1-(3-methoxybenzyl)-1,5-dihydro-2H-pyrrol-2-one |
| 92 | 4-acetyl-1-(3,5-difluorobenzyl)-3-hydroxy-5-phenyl-1,5-dihydro-2H-pyrrol-2-one |
| 93 | 4-acetyl-1-(3,5-difluorobenzyl)-5-(4-fluorophenyl)-3-hydroxy-1,5-dihydro-2H-pyrrol-2-one |
| 94 | 4-acetyl-1-(3,5-difluorobenzyl)-3-hydroxy-5-(4-methylphenyl)-1,5-dihydro-2H-pyrrol-2-one |
| 95 | 4-acetyl-1-benzyl-3-hydroxy-5-neopentyl-1,5-dihydro-2H-pyrrol-2-one |
| 96 | 4-acetyl-1-benzyl-3-hydroxy-5-(3,3,3-trifluoropropyl)-1,5-dihydro-2H-pyrrol-2-one |
| 97 | 4-acetyl-5-cyclohexyl-1-(3-fluorophenyl)-3-hydroxy-1,5-dihydro-2H-pyrrol-2-one |
| 98 | 4-butyryl-5-cyclohexyl-3-hydroxy-1-(4-methylphenyl)-1,5-dihydro-2H-pyrrol-2-one |
| 99 | 4-acetyl-1-cyclohexyl-3-hydroxy-5-(4-methylphenyl)-1,5-dihydro-2H-pyrrol-2-one |
| 100 | 5-cyclohexyl-4-hexanoyl-3-hydroxy-1-(4-methylphenyl)-1,5-dihydro-2H-pyrrol-2-one |
| 101 | 1-(4-chlorophenyl)-5-cyclohexyl-3-hydroxy-4-(3-phenylpropanoyl)-1,5-dihydro-2H-pyrrol-2-one |
| 102 | 1-(4-bromophenyl)-5-cyclohexyl-3-hydroxy-4-(3-phenylpropanoyl)-1,5-dihydro-2H-pyrrol-2-one |
| 103 | 1-(4-chlorophenyl)-5-cyclohexyl-4-hexanoyl-3-hydroxy-1,5-dihydro-2H-pyrrol-2-one |
| 104 | 1-(4-chlorophenyl)-5-cyclohexyl-3-hydroxy-4-pentanoyl-1,5-dihydro-2H-pyrrol-2-one |
| 105 | 4-acetyl-5-cyclohexyl-1-(4-fluoro-3-nitrophenyl)-3-hydroxy-1,5-dihydro-2H-pyrrol-2-one |
| 106 | 4-acetyl-3-hydroxy-1-(4-methylphenyl)-5-(thien-3-yl)-1,5-dihydro-2H-pyrrol-2-one |
| 107 | 4-acetyl-1-(3-bromo-4-methylphenyl)-3-hydroxy-5-propyl-1,5-dihydro-2H-pyrrol-2-one |
| 108 | 4-acetyl-1-(3,4-dimethylphenyl)-3-hydroxy-5-isobutyl-1,5-dihydro-2H-pyrrol-2-one |
| 109 | 4-acetyl-1-(3-fluoro-4-methylphenyl)-3-hydroxy-5-propyl-1,5-dihydro-2H-pyrrol-2-one |
| 110 | 4-acetyl-1-(3-fluoro-4-methylphenyl)-3-hydroxy-5-pentyl-1,5-dihydro-2H-pyrrol-2-one |
| 111 | 4-acetyl-1-(3-chloro-4-methylphenyl)-3-hydroxy-5-pentyl-1,5-dihydro-2H-pyrrol-2-one |
| 112 | 4-acetyl-1-(3-chloro-4-methylphenyl)-3-hydroxy-5-isobutyl-1,5-dihydro-2H-pyrrol-2-one |
| 113 | 4-acetyl-1-(2,3-dihydro-1H-inden-5-yl)-3-hydroxy-5-pentyl-1,5-dihydro-2H-pyrrol-2-one |
| 114 | 4-acetyl-3-hydroxy-1-(3-methylphenyl)-5-neopentyl-1,5-dihydro-2H-pyrrol-2-one |
| 115 | 4-acetyl-1-(3-bromo-4-methylphenyl)-3-hydroxy-5-(3,3,3-trifluoropropyl)-1,5-dihydro-2H-pyrrol-2-one |
| 116 | 4-acetyl-1-(3,4-dimethylphenyl)-3-hydroxy-5-neopentyl-1,5-dihydro-2H-pyrrol-2-one |
| 117 | 4-acetyl-1-(3,4-dimethylphenyl)-3-hydroxy-5-(thien-3-yl)-1,5-dihydro-2H-pyrrol-2-one |
| 118 | 4-acetyl-1-(4-chlorophenyl)-5-cyclopentyl-3-hydroxy-1,5-dihydro-2H-pyrrol-2-one |
| 119 | 4-acetyl-1-(4-chloro-2-fluorophenyl)-5-cyclopentyl-3-hydroxy-1,5-dihydro-2H-pyrrol-2-one |
| 120 | 4-acetyl-1-(4-chloro-2,6-difluorophenyl)-5-cyclohexyl-3-hydroxy-1,5-dihydro-2H-pyrrol-2-one |
| 121 | 4-acetyl-5-bicyclo[2.2.1]hept-5-en-2-yl-1-(4-chlorophenyl)-3-hydroxy-1,5-dihydro-2H-pyrrol-2-one |
| 122 | 4-benzoyl-1-benzyl-3,5-dihydroxy-5-phenyl-1,5-dihydro-2H-pyrrol-2-one |
| 123 | 4-acetyl-1-benzyl-5-ethyl-3-hydroxy-1,5-dihydro-2H-pyrrol-2-one |
| 124 | 4-acetyl-1-benzyl-5-(2,4-dichlorophenyl)-3-hydroxy-1,5-dihydro-2H-pyrrol-2-one |
| 125 | (R)-4-acetyl-1-(4-chloro-2-fluorophenyl)-5-cyclohexyl-3-hydroxy-1,5-dihydro-2H-pyrrol-2-one |
| 126 | 2-cyclohexyl-4-hydroxy-N-methyl-1-(4-methylphenyl)-5-oxo-2,5-dihydro-1H-pyrrole-3-carboxamide |
| 127 | 4-acetyl-1-(4-chlorophenyl)-3-hydroxy-5-(4-methylenecyclohexyl)-1,5-dihydro-2H-pyrrol-2-one |
| 128 | 1-(4-chlorophenyl)-5-cyclohexyl-3-hydroxy-4-(methylthio)-1,5-dihydro-2H-pyrrol-2-one |
| 129 | (R)-4-acetyl-1-(4-chloro-2-fluorophenyl)-5-cyclopentyl-3-hydroxy-1,5-dihydro-2H-pyrrol-2-one |
| 130 | (S)-4-acetyl-1-(4-chloro-2-fluorophenyl)-5-cyclopentyl-3-hydroxy-1,5-dihydro-2H-pyrrol-2-one |
| 131 | 2-cyclohexyl-4-hydroxy-1-(4-methylphenyl)-5-oxo-2,5-dihydro-1H-pyrrole-3-carboxamide |
| 132 | 4-acetyl-1-(4-chlorophenyl)-3-hydroxy-5-(4-methoxycyclohexyl)-1,5-dihydro-2H-pyrrol-2-one |
| 133 | 5-cyclohexyl-3-hydroxy-1-(4-methylphenyl)-4-pent-4-enoyl-1,5-dihydro-2H-pyrrol-2-one |
| 134 | 4-acetyl-1-(4-chlorophenyl)-5-(cyclopentylmethyl)-3-hydroxy-1,5-dihydro-2H-pyrrol-2-one |
| 135 | (R)-4-acetyl-1-(4-chloro-3-methylphenyl)-5-cyclopentyl-3-hydroxy-1,5-dihydro-2H-pyrrol-2-one |
| 136 | 4-acetyl-1-(4-chlorophenyl)-3-hydroxy-5-(4-methoxycyclohexyl)-1,5-dihydro-2H-pyrrol-2-one |
| 137 | (R)-4-acetyl-5-cyclopentyl-1-(4-fluorophenyl)-3-hydroxy-1,5-dihydro-2H-pyrrol-2-one |
| 138 | 4-acetyl-1-(4-chlorophenyl)-5-(1,4-dioxaspiro[4.5]dec-8-yl)-3-hydroxy-1,5-dihydro-2H-pyrrol-2-one |
| 139 | (R)-4-acetyl-5-cyclohexyl-1-(4-fluorophenyl)-3-hydroxy-1,5-dihydro-2H-pyrrol-2-one |
| 140 | (R)-4-acetyl-1-(4-bromophenyl)-5-cyclohexyl-3-hydroxy-1,5-dihydro-2H-pyrrol-2-one |
| 141 | 4-acetyl-1-(4-chlorophenyl)-3-hydroxy-5-(3-noradamantyl)-1,5-dihydro-2H-pyrrol-2-one |
| 142 | 4-acetyl-1-(4-bromo-2-fluorophenyl)-5-cyclohexyl-3-hydroxy-1,5-dihydro-2H-pyrrol-2-one |
| 143 | 5-cyclohexyl-3-hydroxy-1-(4-methylphenyl)-4-[5-(5-methyl-2-phenyl-1,3-oxazol-4-yl)pentanoyl]-1,5-dihydro-2H-pyrrol-2-one |
| 144 | (R)-4-acetyl-1-(4-chlorophenyl)-5-cyclopentyl-3-hydroxy-1,5-dihydro-2H-pyrrol-2-one |
| 145 | 4-acetyl-1-(4-chlorophenyl)-3-hydroxy-5-(3,3,5,5-tetramethylcyclohexyl)-1,5-dihydro-2H-pyrrol-2-one |
| 146 | 5-cyclohexyl-3-hydroxy-1-(4-methylphenyl)-4-[(4E)-5-(5-methyl-2-phenyl-1,3-oxazol-4-yl)pent-4-enoyl]-1,5-dihydro-2H-pyrrol-2-one |

| Cpd. No. | Name |
|---|---|
| 147 | (S)-4-acetyl-1-(4-chloro-2,6-difluorophenyl)-5-cyclohexyl-3-hydroxy-1,5-dihydro-2H-pyrrol-2-one |
| 148 | (R)-4-acetyl-1-(4-chloro-2,6-difluorophenyl)-5-cyclohexyl-3-hydroxy-1,5-dihydro-2H-pyrrol-2-one |
| 149 | (R)-4-acetyl-1-(4-bromo-2-fluorophenyl)-5-cyclohexyl-3-hydroxy-1,5-dihydro-2H-pyrrol-2-one |
| 150 | 4-acetyl-1-(4-chlorophenyl)-3-hydroxy-5-(4-methylcyclohexyl)-1,5-dihydro-2H-pyrrol-2-one |
| 151 | 4-acetyl-1-(4-chloro-2-fluorophenyl)-3-hydroxy-5-(3-noradamantyl)-1,5-dihydro-2H-pyrrol-2-one |
| 152 | 4-acetyl-5-(4-tert-butylcyclohexyl)-1-(4-chlorophenyl)-3-hydroxy-1,5-dihydro-2H-pyrrol-2-one |
| 153 | 4-acetyl-1-(4-chloro-2-fluorophenyl)-3-hydroxy-5-(4-methylenecyclohexyl)-1,5-dihydro-2H-pyrrol-2-one |
| 154 | 4-acetyl-1-(4-bromo-2,6-difluorophenyl)-5-cyclohexyl-3-hydroxy-1,5-dihydro-2H-pyrrol-2-one |
| 155 | (R)-4-acetyl-1-(4-bromo-2,6-difluorophenyl)-5-cyclohexyl-3-hydroxy-1,5-dihydro-2H-pyrrol-2-one |
| 156 | (R)-4-acetyl-1-(4-chlorophenyl)-3-hydroxy-5-tricyclo[3.3.1.0~3,7~]non-3-yl-1,5-dihydro-2H-pyrrol-2-one |
| 157 | 4-acetyl-1-(4-chlorophenyl)-5-cyclohexyl-3-mercapto-1,5-dihydro-2H-pyrrol-2-one |
| 158 | 1-(4-chlorophenyl)-4-(cyclohexylcarbonyl)-3-hydroxy-1,5-dihydro-2H-pyrrol-2-one |
| 159 | 4-acetyl-5-(4-fluorophenyl)-3-hydroxy-1-(4-methylphenyl)-1,5-dihydro-2H-pyrrol-2-one |
| 160 | 4-acetyl-3-hydroxy-1-(4-methylphenyl)-5-phenyl-1,5-dihydro-2H-pyrrol-2-one |
| 161 | (S)-4-acetyl-5-cyclohexyl-3-hydroxy-1-(4-methylphenyl)-1,5-dihydro-2H-pyrrol-2-one |
| 162 | methyl 2-cyclohexyl-4-hydroxy-1-(4-methylphenyl)-5-oxo-2,5-dihydro-1H-pyrrole-3-carboxylate |
| 163 | (S)-4-acetyl-1-(4-chlorophenyl)-5-cyclohexyl-3-hydroxy-1,5-dihydro-2H-pyrrol-2-one |
| 164 | 1-(4-bromophenyl)-5-cyclohexyl-4-hexanoyl-3-hydroxy-1,5-dihydro-2H-pyrrol-2-one |
| 165 | ethyl 2-cyclohexyl-4-hydroxy-1-(4-methylphenyl)-5-oxo-2,5-dihydro-1H-pyrrole-3-carboxylate |
| 166 | N-(3-chlorophenyl)-2-cyclohexyl-4-hydroxy-1-(4-methylphenyl)-5-oxo-2,5-dihydro-1H-pyrrole-3-carboxamide |
| 167 | N-butyl-2-cyclohexyl-4-hydroxy-1-(4-methylphenyl)-5-oxo-2,5-dihydro-1H-pyrrole-3-carboxamide |
| 168 | 2-cyclohexyl-4-hydroxy-1-(4-methylphenyl)-5-oxo-2,5-dihydro-1H-pyrrole-3-carboxamide |
| 169 | 4-acetyl-1-(4-chloro-2-fluorophenyl)-5-cyclohexyl-3-sulfanyl-1,5-dihydro-2H-pyrrol-2-one |

\* \* \* \* \*